(12) United States Patent
Wiggermann et al.

(10) Patent No.: US 10,127,788 B2
(45) Date of Patent: Nov. 13, 2018

(54) ESTIMATION AND MONITORING OF PATIENT TORSO ANGLE

(71) Applicant: Hill-Rom Services, Inc., Batesville, IN (US)

(72) Inventors: Neal Wiggermann, Batesville, IN (US); Charles A. Lachenbruch, Batesville, IN (US); Timothy J. Receveur, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 15/827,277

(22) Filed: Nov. 30, 2017

(65) Prior Publication Data

US 2018/0089979 A1    Mar. 29, 2018

Related U.S. Application Data

(63) Continuation of application No. 15/053,436, filed on Feb. 25, 2016, now Pat. No. 9,836,942.

(60) Provisional application No. 62/152,105, filed on Apr. 24, 2015.

(51) Int. Cl.
| | |
|---|---|
| *G08B 21/04* | (2006.01) |
| *A61B 5/107* | (2006.01) |
| *A61B 5/11* | (2006.01) |
| *G08B 25/08* | (2006.01) |
| *G08B 3/10* | (2006.01) |

(52) U.S. Cl.
CPC ........ *G08B 21/0446* (2013.01); *A61B 5/1071* (2013.01); *A61B 5/1115* (2013.01); *A61B 5/1117* (2013.01); *A61B 5/1118* (2013.01); *G08B 21/0461* (2013.01); *G08B 25/08* (2013.01); *G08B 3/10* (2013.01)

(58) Field of Classification Search
CPC combination set(s) only.
See application file for complete search history.

(56) References Cited

U.S. PATENT DOCUMENTS

| | | | |
|---|---|---|---|
| 2,403,420 | A | 7/1946 | Willingham |
| 4,578,980 | A | 4/1986 | Beckman |
| 4,769,584 | A | 9/1988 | Irigoyen et al. |
| 5,082,357 | A | 1/1992 | Hass et al. |
| 5,181,288 | A | 1/1993 | Heaton et al. |
| 5,205,004 | A | 4/1993 | Hayes et al. |

(Continued)

*Primary Examiner* — Travis R Hunnings
(74) *Attorney, Agent, or Firm* — Barnes & Thornburg LLP

(57) ABSTRACT

A person support apparatus supports a person in a laying-down or a seated position. One or more body-mounted sensors detect changes in the position of the person relative to a reference. A control system receives output from the body-mounted sensor or sensors through a remote coupling. The control system uses patient position information obtained from the body-mounted sensors to determine whether the person has experienced a change-in-position and/or a change-in-activity event. Alternatively or in addition, the position of the person situated on a person support apparatus is detected using one or more sensors that are not body-mounted, but rather are coupled to the person support apparatus or to another component of a patient support system. The patient position information is used to estimate the patient's torso angle. The estimated torso angle is used to assess the patient's condition.

20 Claims, 13 Drawing Sheets

(56) References Cited

U.S. PATENT DOCUMENTS

| | | |
|---|---|---|
| 5,611,096 A | 3/1997 | Bartlett et al. |
| 5,673,443 A | 10/1997 | Marmor |
| 5,715,548 A | 2/1998 | Weismiller et al. |
| 5,732,423 A | 3/1998 | Weismiller et al. |
| 5,822,813 A | 10/1998 | Powell |
| 6,014,784 A | 1/2000 | Taylor et al. |
| 6,185,767 B1 | 2/2001 | Brooke et al. |
| 6,336,235 B1 | 1/2002 | Ruehl |
| 6,353,949 B1 | 3/2002 | Falbo |
| 6,353,950 B1 | 3/2002 | Bartlett et al. |
| 6,356,203 B1 | 3/2002 | Halleck et al. |
| 6,397,716 B1 | 6/2002 | Garuglieri |
| 6,505,365 B1 | 1/2003 | Hanson et al. |
| 6,566,833 B2 | 5/2003 | Bartlett |
| 6,694,549 B2 | 2/2004 | Perez et al. |
| 6,708,358 B2 | 3/2004 | Hensley |
| 6,904,631 B2 | 6/2005 | Vrzalik et al. |
| 7,089,612 B2 | 8/2006 | Rocher et al. |
| 7,117,607 B2 | 10/2006 | Horgan |
| 7,325,265 B2 | 2/2008 | Hornbach et al. |
| 7,454,805 B2 | 11/2008 | Osborne et al. |
| 7,458,119 B2 | 12/2008 | Hornbach et al. |
| 7,487,562 B2 | 2/2009 | Frondorf et al. |
| 7,523,515 B2 | 4/2009 | Allen et al. |
| 7,562,458 B1 | 7/2009 | Clark, Jr. et al. |
| 7,610,637 B2 | 11/2009 | Menkedick et al. |
| 7,610,638 B2 | 11/2009 | Kramer et al. |
| 7,784,128 B2 | 8/2010 | Kramer |
| 7,934,321 B2 | 5/2011 | Johnson et al. |
| 8,051,513 B2 | 11/2011 | Reed et al. |
| 8,063,785 B2 | 11/2011 | Sacchetti |
| 8,108,957 B2 | 2/2012 | Richards et al. |
| 8,146,187 B2 | 4/2012 | Lachenbruch et al. |
| 8,155,918 B2 | 4/2012 | Reed et al. |
| 8,266,741 B2 | 9/2012 | Penninger et al. |
| 8,266,742 B2 | 9/2012 | Andrienko |
| 8,266,743 B2 | 9/2012 | Jones et al. |
| 8,437,876 B2 | 5/2013 | Receveur et al. |
| 8,516,630 B2 | 8/2013 | Gugliotti et al. |
| 8,519,852 B2 | 8/2013 | Johnson et al. |
| 8,584,279 B2 | 11/2013 | Richards et al. |
| 8,617,098 B2 | 12/2013 | Gerber |
| 8,682,457 B2 | 3/2014 | Rawls-Meehan |
| 8,836,515 B2 | 9/2014 | Albert et al. |
| 8,866,620 B2 * | 10/2014 | Amir .................... G08B 21/043 340/573.1 |
| 8,869,328 B2 | 10/2014 | Rawls-Meehan |
| 8,882,684 B2 * | 11/2014 | Halperin ................ A61B 5/002 600/300 |
| 8,909,357 B2 | 12/2014 | Rawls-Meehan |
| 8,926,535 B2 | 1/2015 | Rawls-Meehan |
| 9,005,101 B1 | 4/2015 | Van Erlach |
| 9,031,673 B2 | 5/2015 | Rawls-Meehan |
| 9,128,474 B2 | 9/2015 | Rawls-Meehan |
| 9,226,593 B2 | 1/2016 | Rawls-Meehan |
| 9,295,338 B2 | 3/2016 | Rawls-Meehan |
| 9,295,600 B2 | 3/2016 | Receveur |
| 9,358,168 B2 * | 6/2016 | Williamson ........... G16H 40/63 |
| 9,836,942 B2 * | 12/2017 | Wiggermann ..... G08B 21/0446 |
| 2002/0091326 A1 * | 7/2002 | Hashimoto ............. A61B 5/11 600/483 |
| 2009/0165207 A1 | 7/2009 | Reed et al. |
| 2010/0071129 A1 * | 3/2010 | Yokota ................ A61G 7/0005 5/83.1 |
| 2013/0090571 A1 * | 4/2013 | Nourani ................ A61B 5/103 600/587 |
| 2013/0267791 A1 * | 10/2013 | Halperin ................ A61B 5/002 600/300 |
| 2016/0314672 A1 | 10/2016 | Wiggermann et al. |
| 2017/0020756 A1 | 1/2017 | Hillenbrand, II et al. |

\* cited by examiner

ESTIMATION AND MONITORING OF PATIENT TORSO ANGLE

The present application is a continuation of U.S. application Ser. No. 15/053,436, filed Feb. 25, 2016, to be issued as U.S. Pat. No. 9,836,942, which claims the benefit, under 35 U.S.C. § 119(e), of U.S. Provisional Patent Application No. 62/152,105, filed Apr. 24, 2015, and each of which is hereby incorporated by reference herein.

BACKGROUND

A person support apparatus, such as a hospital bed, stretcher, or similar device, may be used to support a person in a number of different positions, including a laying-down position and/or a seated position. Such a product may be found, for example, in healthcare facilities, homes, and/or other locations in which patient care is provided. The person support apparatus can be equipped with technology, such as an articulating head section or Reverse Trendelenburg functionality, that elevates the patient's head and upper torso region relative to the rest of the patient's body. Sensors can be used to monitor the position of the person support apparatus or the body position of the patient.

SUMMARY

The present disclosure describes a number of features that may be recited in the appended claims and which, alone or in any combination, may comprise patentable subject matter. According to at least one aspect of this disclosure, a method for monitoring the body position of a person supported by a person support apparatus includes, with a control module to control the person support apparatus, monitoring body position signals from a sensor mounted to the person, where the body position signals indicate a position of the person relative to gravity; monitoring bed status signals from one or more bed status sensors of the person support apparatus, where the bed status signals indicate an operational status of the person support apparatus; and determining, based on the body position signals and the bed status signals, whether the person has experienced an event warranting attention.

The method may include deriving, from the body position signals, an angle of the person's torso relative to gravity; determining, from the bed status signals, an angle of a head section of the person support apparatus relative to horizontal, and determining, based on the angle of the person's torso and the angle of the head section of the person support apparatus, whether the event has occurred. The method may include deriving, from the body position signals, a degree of lateral rotation of the person's torso; determining, from the bed status signals, a status of a rotation therapy provided by a support surface of the person support apparatus, and determining, based on the lateral rotation of the person's torso and the status of the rotation therapy, whether the event has occurred. The method may include deriving, from the body position signals, an indication of movement of the person's torso along the length of the person support apparatus over time, and determining whether the event has occurred based on the amount of movement of the person's torso along the length of the person support apparatus over time. The method may include deriving, from the body position signals, an indication of the location of the person's body as a whole relative to a zone of a support surface of the person support apparatus and determining, based on the location of the person's body as a whole, whether the event has occurred. The method may include deriving, from the body position signals, an indication of the person's level of physical activity and determining, based on the person's level of activity, whether the event has occurred. The method may include monitoring reference signals from a reference sensor mounted to the person support apparatus, comparing the body position signals to the reference signals, and using the difference between the reference signals and the body position signals to determine whether the event has occurred. The method may include receiving, by a remote coupling, the body position signals and the reference signals at a receiver mounted to the person support apparatus. The method may include receiving, by a remote coupling, the body position signals at a receiver mounted to the person support apparatus.

According to at least one aspect of this disclosure, a body position monitor for a person supported by a bed is embodied in a control unit of the bed to detect patient change in position events by: receiving a body position signal from a body-mounted position sensor, where the body-mounted position sensor is coupled to a body portion of a person supported by the person support apparatus and is remotely coupled to the bed, and the patient position signal indicates a position of the body portion relative to the bed; receiving a bed position signal from the bed, where the bed position signal indicates a position of a section of the bed supporting the body portion of the person; and determining whether the person has experienced a change in position event warranting attention based on the body position signal and the bed position signal.

The body position monitor may receive a plurality of body position signals from the body-mounted sensor over time, and determine from the body position signals whether the person has experienced the change in position event. The body position monitor may determine from the body position signals whether the person has slid down along the length of the bed. The body position monitor may receive a plurality of body position signals from a plurality of body-mounted position sensors coupled to a plurality of different body portions of the person, and determine from the body position signals and the bed position signals whether the person has assumed a position relative to the bed that warrants attention. The body position monitor may receive a plurality of body position signals from a plurality of body-mounted position sensors coupled to a plurality of different body portions of the person, and determine from the body position signals and the bed position signals whether the person's level of activity relative to the bed warrants attention. The body position monitor may determine from the body position signals and the bed position signals whether the person has rolled onto the person's side independently of any turning or rotation therapy feature of the bed. The body position monitor may determine from the body position signals and the bed position signals whether the person has fallen out of the bed.

According to at least one aspect of this disclosure, a person support system includes a person support apparatus to support a person in a plurality of positions including a horizontal position; a receiver mounted to the person support apparatus to receive person position signals from a body-mounted sensor, where the body-mounted sensor is mounted to the person and remotely coupled to the receiver; and a control module to receive bed status signals from the person support apparatus, where the bed status signals indicate an operational status of the person support apparatus. The method may derive from the person position signals an indication of the position of the person relative to the person support apparatus, and control operation of the person support apparatus based on the derived position of the person relative to the person support apparatus and the bed status signals.

The person support system may include a plurality of receivers mounted to the person support apparatus at different locations, where the control module is configured to derive from the person position signals received at the plurality of receivers the indication of the position of the person relative to the person support apparatus. The plurality of receivers may receive person position signals from a plurality of body-mounted sensors mounted to different parts of the person, and the control module may derive the indication of the person's position relative to the bed based on the person position signals from the plurality of body-mounted sensors. The person support system may include a plurality of reference sensors coupled to the bed at different locations, where the receivers receive reference signals from the reference sensors and the control module may use the reference signals to determine the position of the person. The control module may determine whether the person has experienced a change in position relative to the bed that warrants attention based on the person position signals and may adjust a turning or rotation therapy provided by the bed in response to the person's change in position.

According to at least one aspect of this disclosure, a person support system includes: a person support apparatus comprising at least a head end and a foot end, wherein a distance between the head end and the foot end defines a length of a support surface of the person support apparatus and at least the head end is pivotable about a transverse axis of the patient support apparatus; and electronics communicatively coupled to the person support apparatus, the electronics to compute a torso angle of a patient positioned on the support surface based on an input indicative of a location of the patient's sacral region along the length of the person support apparatus, the torso angle formed by an intersection of a plane extending from the patient's shoulders to the patient's hips with a plane extending substantially horizontally from the patient's hips.

The electronics may compute the torso angle by comparing the location of the patient's sacral region to a reference location located along the length of the person support apparatus. The electronics may determine a migrated distance extending between the location of the patient's sacral region and the reference location, and estimate the torso angle based on the migrated distance. The electronics may (i) determine a migrated distance extending between the location of the patient's sacral region and the reference location, (ii) determine a head of bed angle, wherein the head of bed angle is formed by an intersection of a plane extending from the head end of the person support apparatus to the transverse axis about which the head end pivots with a plane extending horizontally from the transverse axis, and (iii) estimate the torso angle based on the migrated distance and the head of bed angle. The reference location may include a visual indicator located on a component of the person support apparatus. The visual indicator may be located on a siderail of the patient support apparatus. The reference location may be substantially aligned with a suggested hip or sacral location of the patient with respect to the length of the person support apparatus. The electronics may determine the torso angle based on a known relationship between longitudinal patient hip or sacral region displacement and torso angle. The person support system may include a sensor coupled to the person support apparatus, wherein the input comprises a signal generated by the sensor, and the electronics are to (i) determine a location of a sacral region of the patient's body based on the sensor signal and (ii) estimate the torso angle of the patient based on the determined location of the sacral region of the patient's body. The person support system may include a sensor coupled to the person support apparatus, wherein the input comprises a signal generated by the sensor, and the electronics are to (i) estimate a location of a sacral region of the patient's body with respect to the person support apparatus based on the sensor signal, (ii) determine a location of the sensor with respect to the person support apparatus, and (iii) estimate the torso angle of the patient based on the location of the sacral region of the patient's body and the location of the sensor. The person support system may include a sensor coupled to the person support apparatus, wherein the input comprises a signal generated by the sensor, and the electronics are to (i) estimate a location of a sacral region of the patient's body with respect to the person support apparatus based on the sensor signal, (ii) determine a location of the sensor with respect to the person support apparatus, (iii) determine a head of bed angle of the head end of the person support apparatus, and (iv) estimate the torso angle of the patient based on the location of the sacral region of the patient's body, the location of the sensor, and the head of bed angle. The sensor may include a sensor array. The sensor may be coupled to: a frame of the person support apparatus, or a mattress supportable by the person support apparatus, or an overlay supportable by the person support apparatus. The person support system may include a plurality of sensors coupled to the person support apparatus, wherein the input comprises signals generated by the plurality of sensors, and the electronics are to (i) determine a location of a sacral region of the patient's body with respect to the person support apparatus based on a first sensor signal, (ii) determine a location of a first shoulder of the patient with respect to the person support apparatus based on a second sensor signal, (iii) determine a location of a second shoulder of the patient with respect to the person support apparatus based on a third sensor signal, and (iii) estimate the torso angle of the patient based on the first, second, and third sensor signals.

According to at least one aspect of this disclosure, a person support apparatus includes: a support surface comprising at least a head end and a foot end, wherein a distance between the head end and the foot end defines a length of the support surface and at least the head end is pivotable about a transverse axis of the support surface; and electronics communicatively coupled to the support surface, the electronics to compute a torso angle of a patient positioned on the support surface based on an input indicative of a location of the patient's sacral region along the length of the support surface, the torso angle formed by an intersection of a plane extending from the patient's shoulders to the patient's hips with a plane extending substantially horizontally from the patient's hips.

The electronics may compute the torso angle by comparing the location of the patient's sacral region to a reference location located along the length of the support surface. The electronics may determine a migrated distance extending between the location of the patient's sacral region and the reference location, and estimate the torso angle based on the migrated distance. The electronics may (i) determine a migrated distance extending between the location of the patient's sacral region and the reference location, (ii) determine a head of bed angle, wherein the head of bed angle is formed by an intersection of a plane extending from the head end of the support surface to the transverse axis about which the head end pivots with a plane extending horizontally from the transverse axis, and (iii) estimate the torso angle based on the migrated distance and the head of bed angle. The reference location may include a visual indicator located on a component of the support surface. The visual indicator may be located on a siderail of the support surface. The reference location may be substantially aligned with a suggested hip or sacral location of the patient with respect to the length of the support surface. The electronics may determine the torso angle based on a known relationship between longitudinal patient hip or sacral region displacement and torso angle. The person support apparatus may include a sensor coupled to the support surface, wherein the input comprises a signal generated by the sensor, and the electronics are to (i) determine a location of a sacral region of the patient's body based on the sensor signal and (ii) estimate the torso angle of the patient based on the determined location of the sacral region of the patient's body. The person support apparatus may include a sensor coupled to the support surface, wherein the input comprises a signal generated by the sensor, and the electronics are to (i) estimate a location of a sacral region of the patient's body with respect to the support surface based on the sensor signal, (ii) determine a location of the sensor with respect to the support surface, and (iii) estimate the torso angle of the patient based on the location of the sacral region of the patient's body and the location of the sensor. The person support apparatus may include a sensor coupled to the support surface, wherein the input comprises a signal generated by the sensor, and the electronics are to (i) estimate a location of a sacral region of the patient's body with respect to the support surface based on the sensor signal, (ii) determine a location of the sensor with respect to the support surface, (iii) determine a head of bed angle of the head end of the support surface, and (iv) estimate the torso angle of the patient based on the location of the sacral region of the patient's body, the location of the sensor, and the head of bed angle. The sensor may include a sensor array. The sensor may be coupled to: a mattress, or a mattress ticking, or a mattress overlay. The person support apparatus may include a plurality of sensors coupled to the support surface, wherein the input comprises signals generated by the plurality of sensors, and the electronics are to (i) determine a location of a sacral region of the patient's body with respect to the support surface based on a first sensor signal, (ii) determine a location of a first shoulder of the patient with respect to the support surface based on a second sensor signal, (iii) determine a location of a second shoulder of the patient with respect to the support surface based on a third sensor signal, and (iii) estimate the torso angle of the patient based on the first, second, and third sensor signals.

According to at least one aspect of this disclosure, a person support system includes: a person support apparatus comprising at least a head end and a foot end, wherein a distance between the head end and the foot end defines a length of a support surface of the person support apparatus and at least the head end is pivotable about a transverse axis of the patient support apparatus; and electronics communicatively coupled to the person support apparatus, the electronics to compute a torso angle of a patient positioned on the support surface based on an input indicative of a location of a body part of the patient along the length of the person support apparatus, the torso angle formed by an intersection of a plane extending from the patient's shoulders to the patient's hips with a plane extending substantially horizontally from the patient's hips. The electronics may compute a torso angle of a patient positioned on the support surface based on an input indicative of a location of an ankle of the patient along the length of the person support apparatus. The electronics may compute a torso angle of a patient positioned on the support surface based on an input indicative of a location of a knee of the patient along the length of the person support apparatus. The electronics may compute a torso angle of a patient positioned on the support surface based on an input indicative of a location of the head of the patient along the length of the person support apparatus.

BRIEF DESCRIPTION OF THE DRAWINGS

The detailed description particularly refers to the following figures, in which.

DETAILED DESCRIPTION

Figure 1:
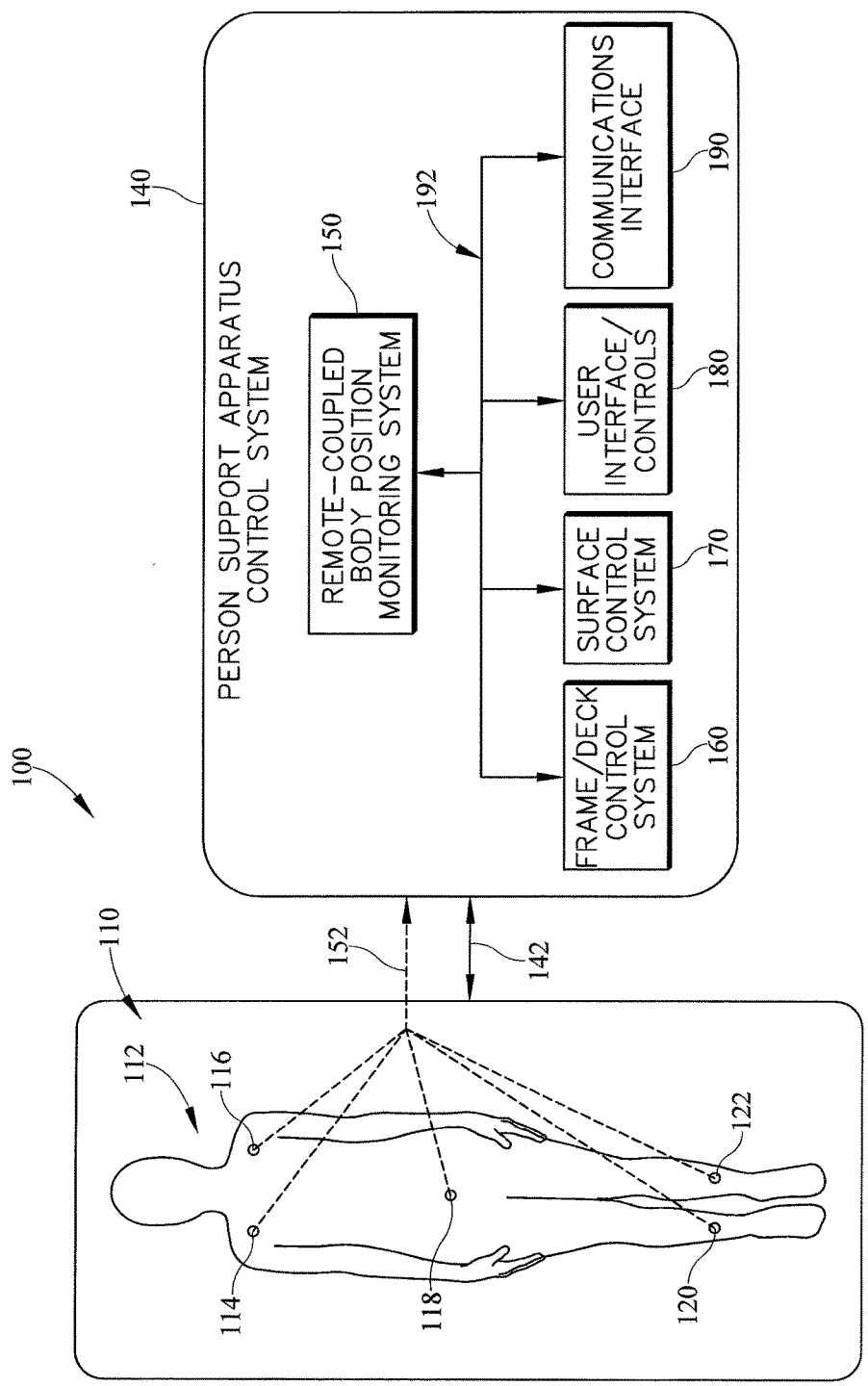
FIG. 1 is a simplified top view of at least one embodiment of a person support system including a person support apparatus, a person with a number of body-mounted sensors situated on the person support apparatus, and, schematically shown, at least one embodiment of a person support apparatus control system in communication with the body-mounted sensors and with the person support apparatus, to monitor the person's position.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

I. Patient Position Monitoring by Remote Coupling of Body-Mounted Sensor

Patient position monitoring systems that rely on bed-based sensors can be limited in that they can determine the position of a person on the bed only indirectly. For example, some bed exit systems may conclude that a patient is about to exit the bed based on the amount of force or pressure detected at an end or edge of the bed, without really knowing, for example, whether the patient is sitting up or laying down on the bed. As another example, head angle monitoring systems may detect the angle of inclination of the head section of the bed and assume the patient's actual head angle corresponds to the angle of the head section of the bed. Further, it may be difficult to tell from the data provided by these types of systems whether, for example, a patient has rolled over onto one's side independently of any turning or lateral rotation features of the bed. For these and other reasons, systems that rely on bed-mounted sensors may give an incomplete picture of the patient's position, movement and activity in relation to the bed. Among other things, these limitations may result in the generation of false alarms, which may cause busy caregivers to waste time responding to unnecessary notifications.

Referring to FIG. 1, a person support system 100 includes a person support apparatus 110 and a person support apparatus control system 140 communicatively coupled to the person support apparatus 10. The person support apparatus 110 is embodied as, for example, a hospital bed, a stretcher, or a similar device that can support a person in a horizontal position and/or one or more non-horizontal positions. The person support apparatus control system 140 is embodied as hardware, software, or a combination of hardware and software, e.g. as a control module or a control unit. The control system 140 controls one or more electronically-controllable features and/or functions of the person support apparatus 110, such as deck articulation, mattress inflation/deflation, and the like. The person support apparatus control system 140 includes a body position monitoring system 150 that collects body position information from one or more remote-coupled sensors 114, 116, 118, 120, 122. The remote-coupled sensors 114, 116, 118, 120, 122 are mounted to a person 112, who may be positioned on the person support apparatus 110. From the sensors 114, 116, 118, 120, 122, the body position monitoring system 150 can obtain detailed information about, for example, the person 112's "real" position relative to some non-bed based reference such as gravity (e.g., sitting up, laying down, etc.), the person 112's position relative to one or more reference points on the person support apparatus 110. Some examples of such "bed-relative" information that may be obtained from one or more of the sensor(s) 114, 116, 118, 120, 122 include: the location of the person's back, shoulders, or feet in relation to the various deck sections or mattress zones of the person support apparatus 110), the amount of the person 112's movement relative to the person support apparatus 110 (e.g., whether the person has rolled over independently of a turning feature of the person support apparatus 110), and the person 112's activity level in relation to the person support apparatus 110 (e.g., the degree, quantity or frequency of active movements over time, with and/or without the assistance of any percussion, vibration, and/or other therapy features provided by the person support apparatus 110).

The person support apparatus control system 140 uses information provided by the body-mounted sensors 114, 116, 118, 120, 122 for a variety of different purposes. In some embodiments, the person support apparatus control system 140 monitors the person 112's torso angle relative to gravity or to the horizontal, based on the data received from one or more of the sensors 114, 116, 118, 120, 122, and uses that information to determine whether to adjust the position of the person support apparatus 110 or adjust (e.g. turn on, turn off, or change a parameter of) a therapy feature of the person support apparatus 110. In some embodiments, the person support apparatus control system 140 uses data received from one or more of the sensors 114, 116, 118, 120, 122 to determine whether the person 112 has slid down in bed to the point that the slide-down event should be brought to the attention of, e.g., a caregiver. By "caregiver," we mean, generally, any person that may care for or attend to the health or medical needs of the person 112, such as a physician, therapist, nurse, family member or friend.

In some embodiments, the person support apparatus control system 140 may evaluate changes in the torso angle or position data obtained from the sensor(s) 114, 116, 118, 120, 122 over time in relation to bed position and/or bed status data, to determine whether the person 112 is falling or has fallen out of bed. In some embodiments, the person support apparatus control system 140 may use the data obtained from the sensor(s) 114, 116, 118, 120, 122 to determine the whole-body position of the person 112 relative to the person support apparatus 110. Such a holistic evaluation of the person 112's body position may be useful, for example, to determine whether the person's body as a whole has assumed an undesirable position even though it may not pose a direct safety risk. For instance, the person 112's body as a whole may be positioned in the center of the person support apparatus 110 and therefore not trigger any bed exit alarms. Nonetheless, the person 112 may be curled up in a fetal position. Such a position may not be reliably detectable by, e.g., frame- or mattress-based force or pressure sensors, but it may, for example, increase the risk of pressure sores, pulmonary issues, muscular atrophy, and/or other health-related issues, and therefore may be of concern. In some embodiments, the person support apparatus control system 140 may evaluate changes in the person 112's activity level based on data obtained from the sensor(s) 114, 116, 118, 120, 122, in relation to bed position and/or bed status data, to determine whether the person 112 is, for example, coughing, moving, or turning without the assistance of the therapy features of the person support apparatus 110.

In more detail, the body-mounted sensor(s) 114, 116, 118, 120, 122 may be embodied as any suitable type of inductive, resistive, or capacitive element (or any combination thereof). Some examples of such sensors include inclinometers, accelerometers, mag sensors, gyroscopes, and/or similar devices, which can be used to collect information about a person's position in space (e.g., the person's angle or position relative to gravity, the Earth's magnetic field, or some other point of reference). Each or any of the sensor(s) 114, 116, 118, 120, 122 may be mounted directly to the person's body (as in the case of electrodes that may be attached to the body with, e.g., adhesive), attached to the person's clothing (e.g., clipped to the person's belt or placed in a pocket), worn by the person (e.g., attached to a tether worn around the person's neck, wrist, or ankles, or as a special piece of clothing, such as a vest), or in any other suitable way. In some embodiments, the body-mounted sensor(s) 114, 116, 118, 120, 122 may be integrated with a mobile computing device (such as a smartphone, tablet-style computer, or other portable electronic device) that is held by the person, clipped to the person's belt, placed in a pocket, or otherwise carried by the person. Illustratively, the sensors 114, 116 are mounted in the region of the person 112's shoulders, the sensor 118 is mounted in the region of the person 112's ilial crest or pelvic region, and the sensors 120, 122 are mounted in the region of the person 112's lower shins. However, it should be understood that the sensor(s) 114, 116, 118, 120, 122 may be placed in any suitable location(s) on the patient 112 as may be needed or desired for a particular design or implementation of the person support system 100.

The output of each of the sensor(s) 114, 116, 118, 120, 122 is operably coupled to a radio transceiver, infrared transmitter, or similar mechanism. For example, the sensor(s) 114, 116, 118, 120, 122 each may be integrated with an RFID (radio-frequency identification) tag or badge, to transmit the data signals from the respective body-mounted sensor(s) 114, 116, 118, 120, 122 to the person support apparatus control system 140 by a remote (e.g., radio frequency, optical, infrared, etc.) coupling 152. In general, the body-mounted sensor(s) 114, 116, 118, 120, 122 and any sensor(s) with which the person support apparatus 110 is equipped may output data signals in discrete or continuous, analog or digital form. The person support apparatus 110 is equipped with appropriate signal processing circuitry and/or devices (e.g. analog-to-digital converters, digital-to-analog converters, filters, and the like) to enable the communication of signals between each of the sensors and the person support apparatus control system 140 and the processing of the signals by the person support apparatus control system 140.

The person support apparatus 110 is in communication with the person support apparatus control system 140 by a two-way data communication link 142. The communication link 142 may be embodied as, for example, any suitable type of wired and/or wireless connection or network, including a Controller Area Network and/or others. The illustrative person support apparatus control system 140 is embodied as a number of computerized sub-systems, modules, programs, or the like, including the remote-coupled body position monitoring system 150, a frame/deck control system 160, a surface control system 170, a user interface/controls sub-system 180, and a communications interface 190. The remote-coupled body position monitoring system analyzes the data signals received from the sensors 114, 116, 118, 120, 122 as described further below. The frame/deck control system 160 and the surface control system 170 control electronically-controllable operational features of the person support apparatus 110, such as head angle adjustment, foot angle adjustment, mattress pressure adjustment, etc., as described further below.

The user interface/controls sub-system 180 provides a user-friendly interface by which a caregiver, the person 112, or another authorized user can review data generated by the various modules of the person support apparatus control system 140, including data generated by the remote-coupled body position monitoring system 150, and adjust or configure the features and/or settings of the person support apparatus 110 based on that data, as may be needed. For instance, the user interface/controls sub-system 180 may process user-supplied inputs from a touch screen graphical display, a microphone, audio speakers, buttons, dials, slides, switches and the like, or any combination thereof and/or other suitable user control mechanisms. The communications interface 190 enables the person support apparatus control system 140 to communicate bi-directionally with other computing systems and/or devices, as described further below. In the illustrative person support apparatus control system 140, the various modules and/or sub-systems 150, 160, 170, 180, 190 are in data communication with each other as illustrated by the bi-directional communication link 192. In this way, body position data collected and analyzed by the remote-coupled body position monitoring system 150, and/or notifications relating thereto, may be displayed or otherwise presented to a caregiver, incorporated into e.g. closed-loop control algorithms for the operation of the person support apparatus 110, or transmitted to a remote device (such as a caregiver's mobile computing device, a nurse's station, or a similar device connected to a healthcare facility's nurse call system).

Figure 2:
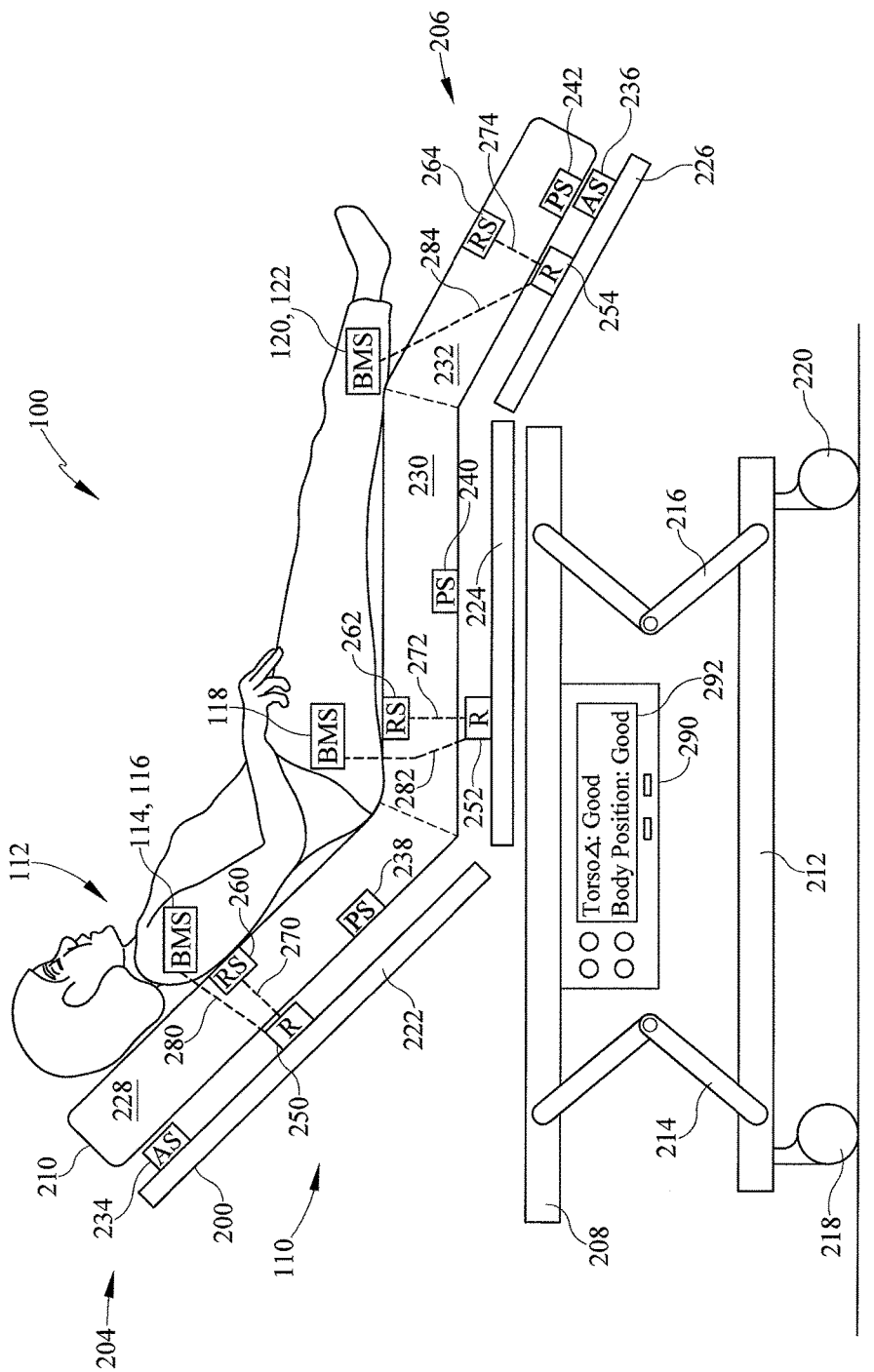
FIG. 2 is a simplified side elevational view of the person support system of FIG. 1 and illustrating some portions of the person support system schematically.
Figure 3:
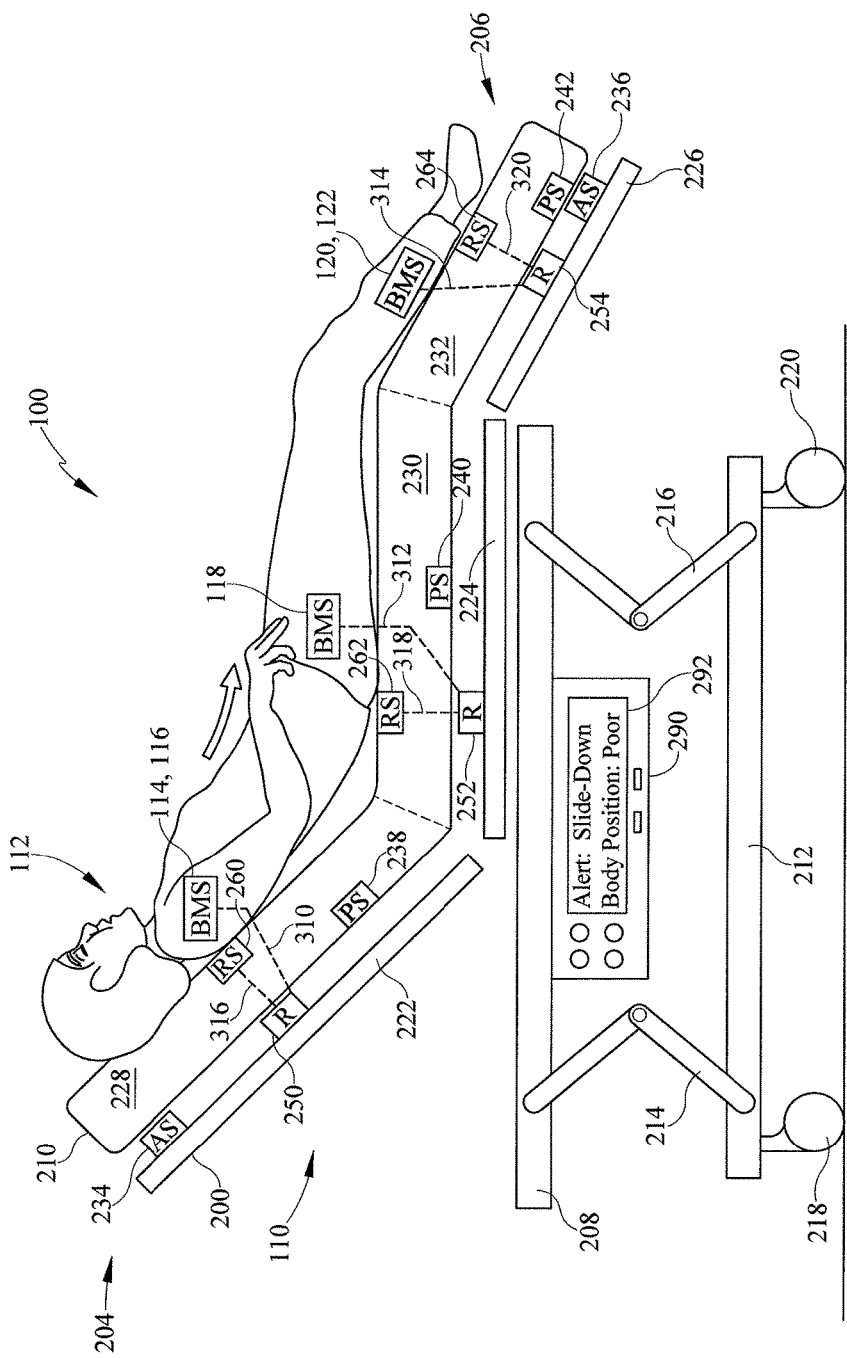
FIG. 3 is a simplified side view similar to FIG. 2, showing the person in a different position from the position of FIG. 2.

Referring now to FIGS. 2-3, the illustrative person support apparatus 110 is shown in more detail. The person support apparatus 110 is shown in a chair-like position, but embodiments of the person support apparatus 110 may be designed to support a person in a laying-down position and/or a variety of other positions, as mentioned above. The illustrative person support apparatus 110 is of a type that is typically used in hospitals and/or other facilities in which health care is provided. However, aspects of this disclosure can be applied to any type of person support apparatus or similar structure, including but not limited to beds, mattresses, cushions, tables, stretchers, chairs, wheelchairs and other similar structures, whether or not all of the features of the illustrated person support apparatus 110 are included in such structure, and whether or not such person support structure includes other features not mentioned herein.

The person support apparatus 110 has a head end 204 and a foot end 206 longitudinally spaced from the head end 104. A base 212 is movably supported by a pair of head end casters 218 (view of one caster obstructed) and a pair of foot end casters 220 (view of one caster obstructed). The casters 218, 220 each include one or more wheels that movably support the person support apparatus 110 relative to a floor or other surface, in one or more directions. A frame 208 is coupled to and supported by the base 212 by a lift mechanism, which includes a pair of head end lift arms 214 (view of one lift arm obstructed by the other) and a pair of foot end lift arms 216 (view of one lift arm obstructed by the other). The lift arms 214, 216 operate to raise, lower, and tilt the frame 208 relative to the base 212. A deck 200 is coupled to and supported by the frame 208. The deck 200 has a number of sections including, in the illustrated embodiment, an articulating head section 222, a seat section 224 (which may also articulate, in some embodiments) and an articulating foot section 226. At least the head section 222 and the foot section 226 pivot relative to the frame 208.

In some embodiments, movement of the lift arms 214, 216 and/or pivoting of the deck sections 222, 224, 226 may be driven by actuators (not shown) that are controlled by the frame/deck control system 160. Some examples of such actuators are such linear actuators or hydraulic cylinders that are responsive to electrical inputs, such as those disclosed in U.S. Pat. Nos. 5,715,548; 6,185,767; 6,336,235; 6,694,549; 7,454,805; 6,708,358; 7,325,265; 7,458,119; 7,523,515; 7,610,637; 7,610,638; and 7,784,128. In general, each of the actuators is coupled to a drive unit (e.g. a motor), which is responsive to control signals issued by the frame/deck control system 160. When movement of the frame 208 or a deck section 222, 224, 226 is requested, the frame/deck control system 160 sends a corresponding control signal or signals to the appropriate drive unit to accomplish the requested movement.

The head and foot sections 222, 226 of the illustrative deck 200 are each equipped with an angle or orientation sensor 234, 236, such as a ball switch, potentiometer, inclinometer, accelerometer, or the like, which detects changes in the orientation of the corresponding section 222, 226 of the deck 200 relative to another section of the person support apparatus 110. For example, the sensors 234, 236 may be used to determine the angle of the head section 222 and the foot section 226, respectively, relative to the frame 208 or to the horizontal. While not specifically shown, similar sensors may be coupled to the frame 208 and/or lift arms 214, 216, to determine the orientation of the frame 208 relative to the horizontal. The frame/deck control system 160 accesses computerized instructions, routines, or the like, which can determine, based on the output of the angle/orientation sensor or sensors, the orientation of the frame 208, the deck 200, and/or a deck section 222, 224, 226, as the case may be.

Also mounted to the illustrative head, seat, and foot sections 222, 224, 226, respectively, of the deck 200 are one or more readers/receivers 250, 252, 254. The readers/receiver(s) 250, 252, 254 are "active" in the sense that each is configured to recognize and/or receive data signals transmitted by the remote-coupled body-mounted sensors 114, 116, 118, 120, 122. As such, the readers/receiver(s) 250, 252, 254 may be embodied as radio-frequency or infrared transceivers, for example. In some embodiments, the readers/receiver(s) 250, 252, 254 may be configured to also recognize and/or receive data signals transmitted by reference sensors 260, 262, 264, which are, illustratively, mounted to, in, or on a support surface 210. For instance, the reference sensors 260, 262, 264 may be installed adjacent a top portion of the each of the zones 228, 230, 232 of the surface 210 as shown in FIGS. 2-3. The readers/receiver(s) 250, 252, 254 communicate the data signals received from the body mounted sensors 114, 116, 118, 120, 122 and the reference sensors 260, 262, 264 to the person support apparatus control system 140 via the communications link 142. While multiple readers/receivers are shown in the illustrated embodiment, it should be understood that in some embodiments, a single reader/receiver may be used and in other embodiments, any number of readers/receivers may be used according to the requirements of a particular design or implementation of the system 100. Moreover, the readers/receiver(s) 250, 252, 254 may be placed in any suitable location or arrangement on the person support apparatus 110 (e.g., near the center or closer to the side edges, or both), including being mounted to the frame or installed in or on the surface 210, as it will be understood that the detection and control algorithms described herein can be adapted based on the selected fixed or known locations of the readers/receiver(s) 250, 252, 254.

The deck 200 supports the support surface 210 (e.g., a mattress), which, in turn, may support the person 112 as shown. Each of the support zones 228, 230, 232 of the surface 210 may include a number of air bladders, foam, a combination thereof and/or other suitable materials. The zone 228 corresponds to the head section 222 of the deck 200, which is configured to support at least the head of the person 112; the zone 230 corresponds to the seat section 224 of the deck 200, which is configured to support at least a back, seat, thigh, and/or torso portion of the person 112; and the zone 232 corresponds to a foot section 226 of the deck 200, which is configured to support at least the legs and/or feet of the person 112. While only three zones are illustrated in FIGS. 2-3, it should be understood that the surface 210 may include any number and configuration of support zones.

In embodiments where the surface 210 includes air bladders, each of the zones 228, 230, 232 includes at least one bladder that is operably coupled to a fluid supply (e.g., a blower) via one or more fluid conduits (e.g., plastic or flexible tubing). At least one pressure sensor 238, 240, 242 is operably coupled to the interior region of each of the zones 228, 230, 232 and/or the fluid conduit connected thereto. The pressure sensors 238, 240, 242 are configured to measure the internal fluid pressure in the zones 228, 230, 232 or individual bladders thereof, as the case may be. The pressure sensors 238, 240, 242 are operably coupled to the surface control system 170 by the communications link 142. As such, the surface control system 170 can continuously monitor the internal air pressure of the zones 228, 230, 232 and interface with the fluid supply to adjust (e.g., increase or decrease) the internal air pressures according to one or more computerized air pressure control routines, which may include, for example, a routine for managing or relieving interface pressures between portions of the person's body and the person support surface 210, a routine for providing one or more pulmonary therapies (such as percussion or vibration), for alternating pressure increases and decreases in different zones or portions thereof (e.g., for lateral rotation or turning assistance), and/or other air pressure control routines.

The person support apparatus 110 also includes a caregiver control unit 290, which is part of the user interface/controls sub-system 180. The illustrative caregiver control unit 290 includes a graphical user interface 292 (e.g., a touchscreen display). The caregiver control unit 290 is, for simplicity, illustrated as being supported by the frame 208. In some embodiments, the caregiver control unit 290 may be integrated with one or more siderails or endboards (e.g., headboard or footboard) of the person support apparatus 110. Alternatively or in addition, the caregiver control unit 190 may be mounted to a wall, headwall, or other vertical structure, or may be embodied as a portable electronic device. In any case, the caregiver control unit 290 receives and processes electrical input (e.g. voltage) from one or more controls coupled thereto, which enable a caregiver to configure, activate and/or deactivate certain of the electronically-controllable functions of the person support apparatus 110. For example, some beds permit the caregiver to raise and lower the frame or change the position of certain deck sections, change the length or width of the frame or deck, to achieve a chair, CPR, Trendelenburg, or reverse Trendelenburg position, and/or to activate certain mattress therapies (such as lateral rotation, percussion, or vibration), by physically contacting the selected control. Such controls may include physical or virtual buttons, switches, dials, slides and the like. For instance, the illustrative caregiver control unit 290 includes a graphical touchscreen user interface 292, which has a display screen that can display text and/or graphics, and a number of interactive controls that allow a caregiver to activate, deactivate, or configure features of the person support apparatus 110. The caregiver control unit 290 includes circuitry to convey voltage generated by the controls mounted thereto to the person support apparatus control system 140.

Some examples of features and functions of the person support apparatus 110 that may be electronically controllable by the caregiver control unit 290 include, but are not limited to: adjusting the position, length, or width of the bed, raising, lowering, or pivoting a section or sections of the bed, weighing a person positioned on the bed, inflating, deflating, or adjusting inflation in one or more sections of the mattress, laterally rotating or turning a person positioned on the bed, providing percussion, vibration, pulsation, or alternating pressure therapy to a person positioned on the bed, adjusting airflow through a portion of a mattress or topper, enabling a person positioned on the bed to communicate with a caregiver located outside the person's room through an electrical network or telecommunications system, exchanging data and/or instructions with other devices, equipment, and/or computer systems (such as a nurse call system or healthcare facility workflow system), and/or other automated features. The above-described electronically controllable features of the person support apparatus 110 are intended to be illustrative and non-exhaustive. It will be understood that other electronically controllable features of the person support apparatus 110 not mentioned herein may be configured in accordance with a person's body position assessment. Although not specifically shown, it should be understood that the person support apparatus 110 has its own supply of electrical power (e.g. a battery) and/or a connector that connects the person support apparatus 110 to a supply of electrical current (e.g. a wall outlet), in order to power the electronically controllable features and functions of the person support apparatus 110.

As shown in FIGS. 2-3, the body-mounted sensor(s) 112, 116, 118, 120, 122 and the reference sensors 260, 262, 264 are remotely coupled to the readers/receiver(s) 250, 252, 254. That is, data signals 270, 272, 274, 280, 282, 284 travel from the reference sensors 250, 252, 254 and body-mounted sensor(s) 112, 114, 116, 118, 220, 222, respectively, through the air and/or other media (e.g., mattress materials) to be received at the readers/receiver(s) 250, 252, 254. In the illustration of FIG. 2, data signals from the body-mounted sensors 114, 116, 118, 120, 122 have been processed by the body position monitoring system 150, alone or in combination with the data signals from the reference sensors 260, 262, 264 and/or the data signals from the sensors 234, 236, 238, 240, 242, and the body position monitoring system 150 has concluded therefrom that the person 112's torso angle is "good" and that the person's overall body position is "good," as shown by the display 292. FIG. 3 is an illustration of a change in the person 112's body position that may occur after an amount of time has passed, e.g., since the system 100's detection of the body position of FIG. 2. In FIG. 3, the person 112 has slid down along the length of the person support apparatus 110 toward the foot end 206. As explained further below, such a slide-down event can be detected by the body position monitoring system 150 by comparing the data signals 310, 312, 314 to the data signals 280, 282, 284 received earlier from the body-mounted sensor(s) 114, 116, 118, 120, 122. In some embodiments, the difference between the signal strengths of the body-mounted sensor data signals 310, 312, 314 and the earlier body-mounted sensor data signals 280, 282, 284, respectively, may be compared to determine the change in the person 112's position. As used herein, "signal strength" may refer to the power level of the signals transmitted by the sensor(s) 114, 116, 118, 120, 122, whether it be electrical or otherwise.

As another example, the difference between the signal strength of the reference data signals 270, 272, 274 and the signal strength of the earlier-received body-mounted sensor data signals 280, 282, 284 may be compared to the difference between the signal strength of the reference data signals 316, 318, 320 and the signal strength of the later-received body-mounted sensor data signals 310, 312, 314, to determine the change in the person 112's position. In FIG. 3, the display 292 reflects the body position monitoring system 150's determination that, based on the body-mounted sensor signals, the person 112 has experienced a slide-down that warrants attention (e.g., by a caregiver) and that the person 112's overall body position is now "poor."

Figure 4:
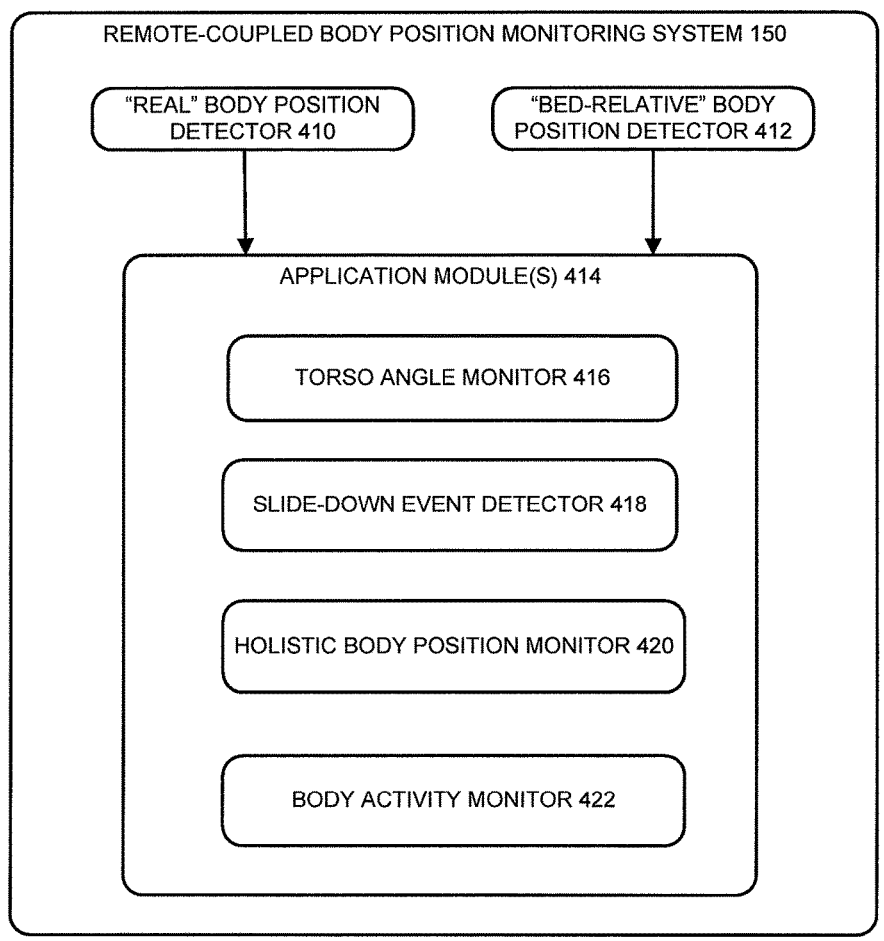
FIG. 4 is a simplified module diagram of at least one embodiment of the remote-coupled body position monitoring system of FIG. 1.

Referring now to FIG. 4, the remote-coupled body position monitoring system 150 is embodied as a number of computerized modules, instructions or routines (e.g., as software, hardware, and/or a combination thereof), including a "real" body position detector 410, a "bed-relative" body position detector 412, and one or more application modules 414. In some embodiments, the real body position detector 410 processes the data signals received from the body-mounted sensor(s) 114, 116, 118, 120, 122 and determines therefrom the "real" body angle and/or body acceleration using, e.g., standard algorithms. As used herein, "real" may refer to a situation in which the angle or acceleration of the person 112's body or a portion thereof is determined relative to some non-bed reference, such as gravity or the horizontal. The output of the body position detector 410 can be used to, for example, sense patient activity and/or the angles of specific body parts of the person 112.

The "bed-relative" body position detector 420 determines the position and/or movement of the person 112's body as compared to some bed-based reference, such as the fixed locations of one or more of the bed-mounted readers/receivers 250, 252, 254. In some embodiments, the bed-relative body position detector 420 determines changes in the person 112's body position by evaluating the signal strength of the data signals received at one or more of the readers/receivers 250, 252, 254 over time. For instance, if the strength of the data signals received by the reader/receiver 250 from the body-mounted sensors 114, 116 decreases over time, the body position detector 412 may conclude that the person 112 has moved further away from the reader/receiver 250. If the reader/receiver 252 then receives signals from the body-mounted sensors 114, 116 that are stronger (e.g., have a greater signal strength) than were previously detected by the reader/receiver 252, then the body position detector 412 may determine that the person 112's shoulders have moved closer to the center of the person support apparatus 110. Further, based on a comparison of the signal strengths detected at both readers/receivers 250, 252, the body position detector 412 may determine that the person 112 has moved down toward the end of the person support apparatus 110 over time. The body position detector 412 may use the data signals from the reference sensors 260, 262, 264 to compensate for noise and/or environmental effects (which may be due to, e.g., the transmission through the surface 210, articulation of the deck, etc.) on the signals transmitted by the body-mounted sensors 114, 116, 118, 120, 122. For example, the body position detector 412 may compare the signal strength of the data signals received from the body-mounted sensors 114, 116, 118, 120, 122 to the signal strength of the data signals received from the reference sensor(s) 260, 262, 264 and use the difference between the two signal strengths as the indicator of body position. For instance, if the difference between the signal strength of the body-mounted sensor 118 and the signal strength of the reference sensor 262 detected at the reader/receiver 252 decreases over time, and the difference between the signal strength of the body mounted sensors 120, 122 and the signal strength of the reference sensor 264 detected at the reader/receiver 254 increases over time, the body position detector 412 may conclude that the person 112's pelvic region has moved longitudinally away from the center of the person support apparatus 112 toward the foot end 206, possibly indicating a slide-down event.

Illustratively, the application modules 414 include a torso angle monitor 416, a slide-down event detector 418, a holistic body position monitor 420, and a body activity monitor 422. Any or all of these modules, and/or other application modules, may be included in various embodiments of the system 150, according to the needs of a particular design or implementation of the system 100. The illustrative torso angle monitor 416 monitors the body angle data detected by the "real" body position detector 410 (e.g., the person 112's head angle relative to gravity), and specifically monitors the torso angle data supplied by e.g., the sensors 114, 116. The torso angle monitor 46 compares the body angle data to one or more defined thresholds, which may be preset or determined through research, testing and/or experimentation, and determines whether the person 112's body angle (or more specifically, the person 112's torso angle) has changed in a way that warrants attention from, e.g., a caregiver.

The illustrative slide-down event detector 418 monitors the "bed-relative" body position data detected by the body position detector 412 over time and converts it to a unit of measurement that can be compared to one or more defined thresholds. For example, a conversion table may be used to convert the differences in signal strength data to a unit of distance (e.g., inches). Such thresholds may be preset or determined through, e.g., research, testing and/or experimentation. Generally, the thresholds are used to determine whether the person's body position has changed in a way that warrants attention from, e.g., a caregiver. In some embodiments, varying degrees of "slide-down" are detected by different threshold values. For example, a movement in the range of 1-3 inches down the length of the person support apparatus 110 may be deemed to constitute a "mild" slide-down event, while a movement in the range of 6 inches down the length of the bed may indicate a "mediocre" slide-down event and a movement greater than 6 inches may indicate a "severe" slide-down event.

The illustrative holistic body position monitor 420 monitors the "bed-relative" body position data detected by the body position detector 412 to determine, at any given time, whether the person 112's body position as a whole is such that it warrants attention from, e.g., a caregiver. For example, the holistic body position monitor 420 may evaluate the distribution of the signal strengths of the data signals from all of the various body mounted sensors 114, 116, 118, 120, 122 across all of the readers/receivers 250, 252, 254 at any given time. If the signal strengths of all of the sensors 114, 116, 118, 120, 122 are detected as high by the reader/receiver 252 and low by the readers/receivers 250, 254, the holistic body position monitor 422 may conclude, for instance, that the person 112 is curled up in a fetal position near the center of the person support apparatus 110.

The illustrative body activity monitor 422 monitors the data signals from the body position detector 410 and/or the data signals from the body position detector 412, over time, and evaluates the person 112's level of activity over the time period. In some cases, the body activity monitor 422 may monitor the changes in the person 112's body angle detected by the body position detector 410 over time to compute acceleration of the person's body (or portion thereof) and determine therefrom whether the person 112 is beginning to fall or is falling out or off of the person support apparatus 110. In some embodiments, the body activity monitor 422 may monitor the data signals from the body position detector 410, the body position detector 420, or both, to determine the person 112's degree and/or frequency of movement over time. The body activity monitor 422 may compare the person 112's body movement data to one or more defined thresholds to determine whether the person 112's level of activity has increased or decreased to the point that it warrants attention from, e.g., a caregiver.

Figure 5:
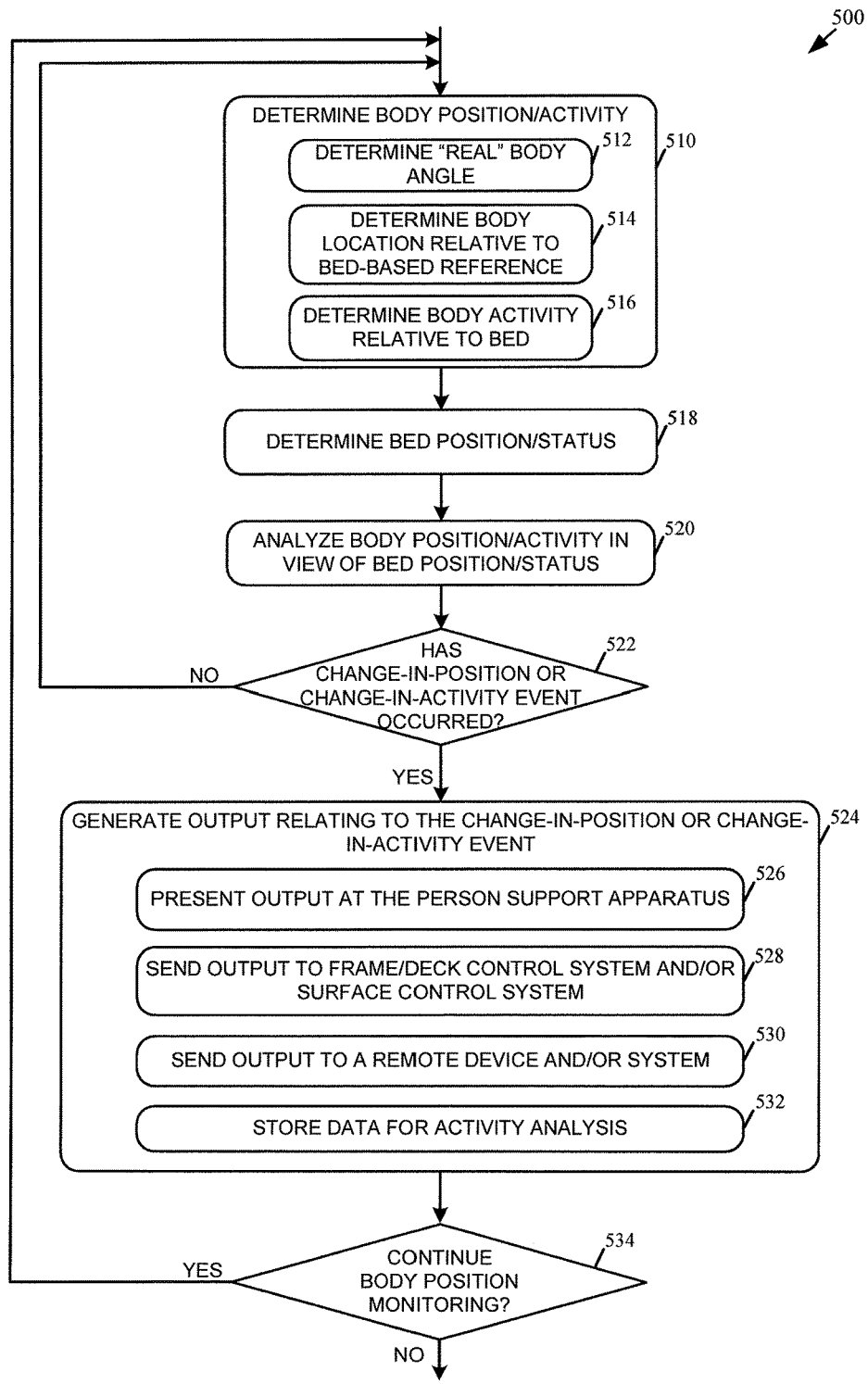
FIG. 5 is a simplified flow diagram of at least one embodiment of a method for monitoring body position.

Referring now to FIG. 5, a method 500 for monitoring the person 112's body position using the body-mounted sensor(s) 114, 116, 118, 120, 122 is shown. The method 500 may be embodied as computerized programs, routines, logic and/or instructions, which may be accessed by a processor, controller, or other computing device. At block 510, the method 500 determines the person 112's current body position and/or level of activity. For instance, in some embodiments, the method 500 determines the person 112's real body angle, as described above, at block 512. In some embodiments, the method 500 determines the person 112's body location to one or more bed-based references (e.g., the readers/receiver(s) 250, 252, 254), at block 514, as described above. In some embodiments, the method 500 analyzes the person 112's level of body activity based on, e.g., a history of body position data obtained from the body-mounted sensor(s) 114, 116, 118, 120, 122 as described above.

At block 518, the method 500 determines the position and/or status of the person support apparatus 110. To do this, the method 500 interfaces with the frame/deck control system 160 and/or the surface control system 170. For instance, block 518 may involve determining the current angle of the head section 222, the current angle of the foot section 224, the current orientation of the frame 208 (e.g., Trend, Reverse Trend, flat), the current status of a surface therapy (e.g., whether a turn assist, lateral rotation, or pulmonary therapy feature is active and/or the parameters of any such active feature), or the current air pressures in one or more of the zones 228, 230, 232 of the surface 210.

At block 520, the method 500 analyzes the person 112's body position in view of the bed position and/or status of the person support apparatus 110. For example, the method 500 may compare the person 112's head angle as detected by the real body position detector 410 to the angle of the head section 222 determined at block 518. As another example, the method 500 may compare the person 112's current body location as detected by the bed-relative body position detector 412 to the current position of the frame 208 and/or the current positions of the deck sections 222, 224, 226. As a further example, the method 500 may compare the person 112's current level of activity to the status of the person support apparatus 110 as determined at block 518. For example, the method 500 may analyze the person 112's current level of activity in view of whether a turn assist, rotation, or pulmonary therapy feature of the person support apparatus 110 is currently or has recently been activated.

At block 522, the method 500 determines, based on the analyses and comparison(s) performed at block 520, whether the person 112's position and/or level of activity has changed so as to indicate that a change-in-position and/or change-in-activity event warranting attention by, e.g., a caregiver, has occurred. To do this, the method 500 may, for example, evaluate the results of the analyses performed at block 520 based on one or more threshold values, as described above. As an example, the method 500 may determine that the person 112's head angle is at an acceptable level even though the angle of the head section 222 is less than a pre-defined acceptable angle, relative to the horizontal. As another example, the method 500 may determine that the person 112's body position is concentrated over the zone 230 of the surface 210, and that this may be cause for concern because the position of the deck 200 and/or the frame 208 hasn't changed in a long while. As a further example, the method 500 may determine based on the data from the body-mounted sensor(s) 114, 116, 118, 120, 122 that the person 112's level of activity is acceptable even though the person support apparatus 112 has not performed turn assist or rotation for a period of time.

If the method 500 determines at block 522 that a change-in-position and/or change-in-activity event warranting attention has not occurred, the method 500 returns to block 510 and continues monitoring the person 112's body position and/or activity in view of the position and/or operational status of the person support apparatus 110. If the method 500 determines at block 522 that a change-in-position and/or change-in-activity event warranting attention has occurred, the method proceeds to block 524, where it generates output relating to the change-in-position and/or change-in-activity event. For instance, in some embodiments, the method 500 presents output, such as a textual or graphical indication of the person's current body angle, position, or status (e.g., "good" or "poor" body position), at block 526. Such presentation may be displayed at the caregiver control unit 290 as shown in FIGS. 2-3, for example. Alternatively or in addition, the presentation of output may include an audio signal such as a beep or a pre-recorded spoken message. In some embodiments, the method 500 may at block 528 send output in the form of control signals to the frame/deck control system 160 and/or the surface control system 170, to adjust the configuration of the person support apparatus 110 in response to the detected change-in-position and/or change-in-activity event. In some embodiments, the method 500 may send output such as an audio or visual notification to a remote electronic device and/or system, at block 530. For example, in some embodiments, data relating to the change-in-position and/or change-in-activity event may be transmitted to an electronic medical records (EMR) system for incorporation into the person 112's medical record. As another example, an alert or notification of the change-in-position and/or change-in-activity event may be transmitted to a caregiver's remote device (e.g., a smart phone, personal digital assistant, VOCERA device, or the like). In some embodiments, data relating to the change-in-position and/or change-in-activity event may, at block 532, be stored in memory at the person support apparatus control system 140 or at another system and used to, e.g., analyze the person 112's level of activity over time, as described above. At block 534, the method 500 determines whether to continue monitoring the person 112's body position, and if so, returns to block 510. Some examples of situations in which the method 500 may discontinue the body position monitoring include situations in which the person 112 has exited the person support apparatus 110 or the body-mounted sensor(s) 114, 116, 118, 120, 122 have been deactivated or removed from the person 112. In such event, the method 500 simply awaits a determination that the person 112 has returned to the person support apparatus 110 or the body-mounted sensor(s) 114, 116, 118, 120, 122 have been reapplied to the person 112, at which point it begins from block 510, again.

Figure 6:
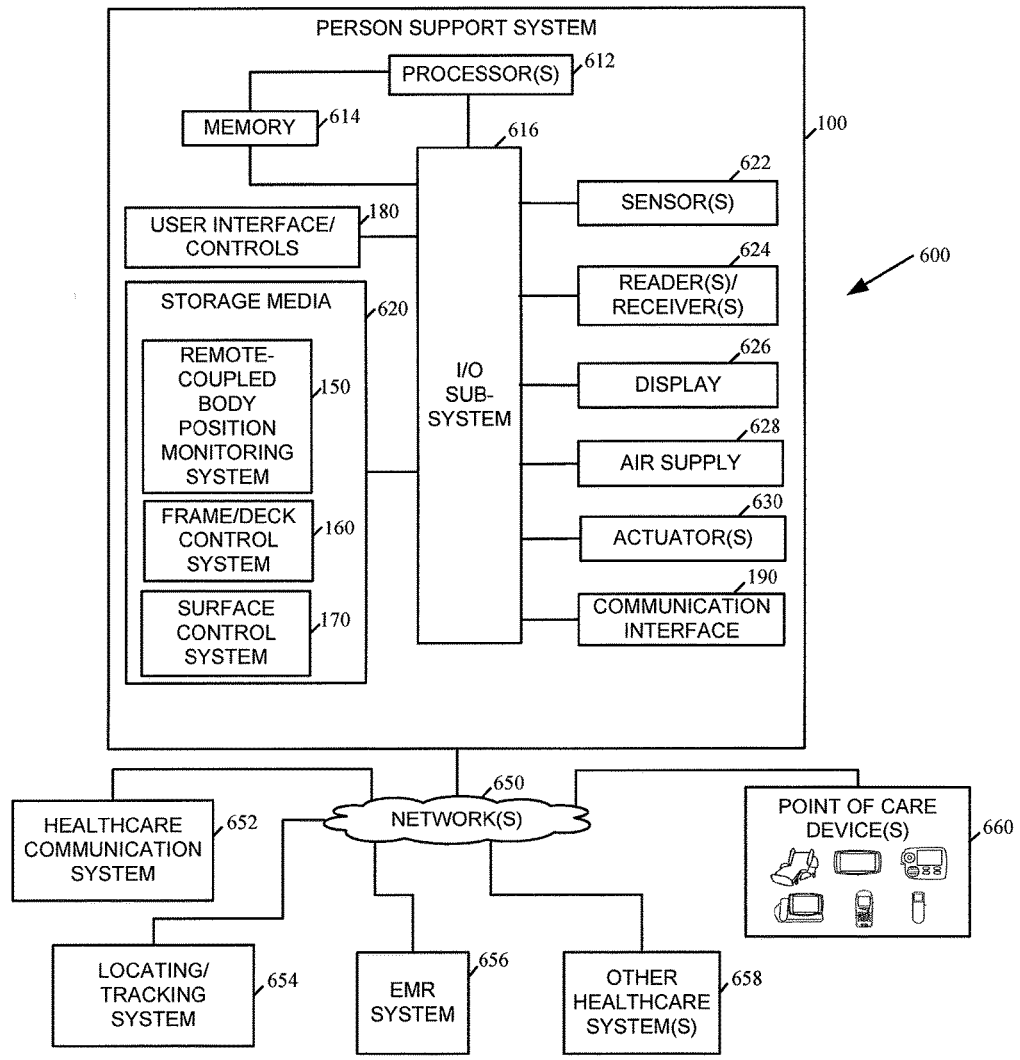
FIG. 6 is a simplified block diagram of at least one embodiment of a computing environment in which the person support system of FIG. 1 may be implemented.

Referring now to FIG. 6, a simplified block diagram of a hardware embodiment 600 of the illustrative person support system 100 is shown. In the illustrative embodiment 600, the person support system 100 is in communication with one or more other computing systems and/or devices 652,654, 656, 658, 650 via one or more networks 650. Illustratively, the remote-coupled body position monitoring system 150 is local to the person support system 100, however, portions thereof may be distributed across one or more of the other computing systems and/or devices 652,654, 656, 658, 650 that are connected to the network(s) 650.

The illustrative person support system 100 includes a number of components, some of which are mounted to the person support apparatus 110, and others of which are remotely coupled to the person support apparatus 110. The embodiment 600 includes at least one processor 612 (e.g. a microprocessor, microcontroller, digital signal processor, etc.), memory 614, and an input/output (I/O) subsystem 616. The person support system 100 and/or portions thereof may be embodied in a control unit of the person support apparatus 110 and/or any type of computing device including a point of care device such as a "nurse's station" or "patient station" of a nurse-call system, a server, a network of computers, or a combination of computers and/or other electronic devices.

The I/O subsystem 616 typically includes, among other things, an I/O controller, a memory controller, and one or more I/O ports. The processor 612 and the I/O subsystem 616 are communicatively coupled to the memory 614. The memory 614 may be embodied as any type of suitable computer memory device (e.g., volatile memory such as various forms of random access memory).

The I/O subsystem 616 is communicatively coupled to a number of hardware and/or software components including the user interface/controls 180, one or more storage media 620, one or more sensors 622 (e.g., the body-mounted sensors 114, 116, 118, 120, 122 and/or sensors 234, 236, 238, 240, 242), one or more readers/receiver(s) 624 (e.g., the readers/receiver(s) 250, 252, 254), a display 626 (e.g., the touchscreen display 292), an air supply 628 (e.g., to control the supply of air to portions of the surface 210), one or more actuators 630 (e.g., to control changes in position of the person support apparatus 110), and the communication interface 190.

The storage media 620 may include one or more hard drives or other suitable data storage devices (e.g., flash memory, memory cards, memory sticks, and/or others). In some embodiments, portions of the body position monitoring system 150, the frame/deck control system 160, and/or the surface control system 170 reside at least temporarily in the storage media 620. Portions of these systems 150, 160, 170 may be copied to the memory 614 during operation of the system 100, for faster processing or other reasons.

The one or more networks 650 may communicatively couple the person support system 100 to a hospital or healthcare facility network, for example. Accordingly, the communication interface 190 may include one or more wired or wireless network interface cards or adapters, for example, as may be needed pursuant to the specifications and/or design of the particular system 100.

The other computing system and devices may include, for example, a healthcare communication system 652 (e.g., a patient-nurse communication system), a locating and tracking system 654 (e.g., a system that monitors the location of caregivers, patients, and/or equipment in a healthcare facility), an EMR system 656, other healthcare system(s) 658 (e.g., an admission, transfer and discharge system), and one or more point of care devices 660 (e.g., other hospital equipment, communication devices, or medical devices). The person support system 100 may include other components, sub-components, and devices not illustrated in FIG. 6 for clarity of the description. In general, the components of the person support system 100 are communicatively coupled as shown in FIG. 6 by electronic signal paths, which may be embodied as any type of wired or wireless signal paths capable of facilitating communication between the respective devices and components.

II. In-Bed Estimation and Monitoring of Patient Torso Angle

A head of bed (HOB) angle as used herein may refer to an angle of elevation of a head end or a head section of a person support apparatus with respect to horizontal. Head elevation can be accomplished by, for example, pivoting the head section or tilting a support surface of the person support apparatus to a Reverse Trendelenburg position. Person support apparatus as used herein may refer to a bed, stretcher, mattress, or other structure configured to support a person in at least a laying down (e.g., supine) position and a position in which the person's head is elevated with respect to the remainder of the person's body.

Research has shown that elevating the HOB can have therapeutic benefits, including reducing the incidence of ventilator-assisted pneumonia (VAP) and reducing aspiration. However, as disclosed herein, raising the HOB elevates the patient's torso, but the HOB angle and the patient's actual torso angle may not coincide. This disclosure recognizes that the patient's torso angle can vary independently of the HOB angle. For example, the patient can migrate down toward the foot end of the bed over time, as a result of the head elevation, to improve comfort, during sleep, or for other reasons. As the patient slides or migrates toward the foot end of the bed, the patient's torso angle changes. Studies conducted in conjunction with this disclosure have shown that even when the HOB angle is set to 30 degrees, the patient's actual torso angle may be as low as 10 degrees, when measured as an amount of incline (or the supplement of 10 degrees, 180–10, when measured as an amount of recline). As a result, even though the HOB angle indicates that the bed is in a "safe" position (e.g., in compliance with VAP protocols), the patient actually may be in a position that puts the patient at risk for VAP or another type of adverse condition. Whereas it is fairly easy to measure and monitor the HOB angle, determining and monitoring the patient's actual torso angle is quite difficult. This disclosure describes technology for measuring the patient's actual torso angle while the patient is positioned on a person support apparatus (e.g. situated in bed). Embodiments described in this disclosure can enable a person support apparatus to monitor the patient's actual torso angle in an automated, non-intrusive way, to provide a number of benefits. For instance, caregivers can use the torso angle information to determine compliance with VAP prevention and/or other protocols.

Figure 7:
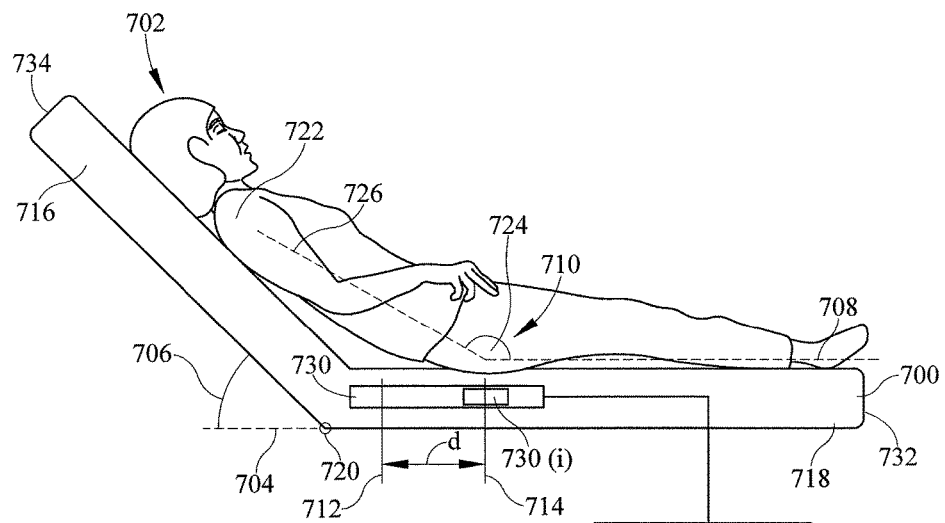
FIG. 7 is a simplified side elevational view of a patient positioned on a person support apparatus, schematically illustrating an embodiment of technology for determining the patient's torso angle.

Referring now to FIG. 7, an embodiment of technology for determining the patient's torso angle is shown. A patient 702 is positioned on a person support apparatus 700. The person support apparatus 700 has at least a lower torso or foot section 718 and an articulating head section 716. A distance between a head end 734 and a foot end 732 defines a length of the person support apparatus 700, e.g., a length of a support surface of the person support apparatus 700. The head section 716 is pivotable about a transverse axis of the person support apparatus 700, which extends into and out of the page at a pivot point 720. The head section 716 is illustratively elevated to a HOB angle 706 with respect to a horizontal axis 704 (e.g., a HOB angle of thirty degrees of incline).

A hip locator 712 (schematically illustrated in FIG. 7) is associated with the person support apparatus 700. The hip locator 712 can be embodied as a visual indicator, such as a printed or engraved marking, a light emitting diode (LED), etc., which is mounted to or supported by a component of the person support apparatus 700. The hip locator 712 is positioned at a location along the length of the person support apparatus 700 that corresponds to a suggested or desired location for the patient's hip or sacral region. The hip locator 712 is positioned to be readily visible to a caregiver attending to the patient 702, e.g., so that the caregiver can easily determine whether the patient has slid down in bed. In the illustration of FIG. 7, the patient's hip 724 is estimated by a sensing element 730(i) to be at a location 714. The distance between the actual hip location 714 and the foot end 732 of the person support apparatus 700 is shorter or smaller than the distance between the hip locator 712 and the foot end 732. Thus, in FIG. 7, the patient's hip or sacral region 724 has migrated toward the foot end 732 by a migrated distance, d.

While the illustrative embodiments utilize the patient's hip or sacral region to estimate migration distance, it should be understood that other body parts can be used, alternatively or in addition. For example, the patient's ankle, knee, or head position and corresponding reference positions could be used as the basis for determining the migration distance d. The person support apparatus 700 can use the migrated distance d to estimate and monitor the patient's actual torso angle 710 (shown in FIG. 7 as a measure of recline; the supplement or measure of incline may be used as the actual torso angle 710 in many embodiments), at discrete time instances or continuously over a time interval. The patient's actual torso angle 710 is defined by an intersection of a plane 726, which extends from the patient's shoulders 722 to the patient's hips or sacral region 724, with a plane 708, which extends substantially horizontally away from the patient's hips or sacral region 724.

The illustrative person support apparatus 700 is equipped with a sensor 730, which is responsive to phenomena introduced by contact of the patient's hip or sacral region 724 with a support surface 740 of the person support apparatus. The sensor 730 may be embodied as a sensor array, e.g., an array of individual sensing elements 730(i), each of which is configured to detect one or more physical phenomena within a discrete, bounded area (e.g., 2 inches by 2 inches), such that the sensor 730 can detect patient migration (as evidenced by changes in the position of the hip or sacral region 724 relative to the length of the patient support apparatus 700) with sufficient particularity.

The phenomena detected by the sensor 730 may include pressure, temperature, motion, moisture, and/or others. For instance, the sensor 730 may be embodied as an array of resistive pressure sensors. The sensor 730 may be coupled to the person support apparatus 700, such as a seat section (e.g., a section of the person support apparatus 700 underlying the hip or sacral region 724 of the patient). For example, the sensor 730 may be supported by a frame member of the person support apparatus 700 (e.g., a seat section of a deck), or embedded in or coupled to a seat section of a mattress, mattress ticking, or mattress overlay. In other embodiments, the sensor 730 may be embodied as an image sensor, e.g., a still or video camera that is set off from the person support apparatus 700 such that the patient 702 and the hip locator 712 are within a field of view of the camera. The camera may capture one or more images of the patient on the person support apparatus 700 over time. Image processing techniques can be used to extract information about the location of patient's hip or sacral region 724 relative to the visual hip locator 712, and compute the migration distance d based on the information extracted from one or more of the images.

In some embodiments, the sensor 730 is embodied as a component of a user interface device, such as a touch sensor of a user interface touchscreen. For instance, a caregiver may utilize a touchscreen to manually input his or her estimation of the migration distance d based on a visual observation or manual measurement of the distance between the hip locator 712 and the actual location of the patient's hip or sacral region 724. In other words, the caregiver may visually estimate the migration distance d and input this information to the person support apparatus 700 via a user interface device.

Irrespective of the sensor type, the sensor 730 outputs one or more sensor signals indicative of the actual location of the patient's hip or sacral region 724. Torso angle electronics 750 receive, pre-process as needed (e.g., perform analog-to-digital conversion, filtering, and/or other signal processing) and analyze the sensor signals. For example, the electronics 750 may access one or more data stores (not shown) to obtain stored information about the location of the hip locator 712 and the location of the sensor 730. When a signal from a particular sensor 730(i) is received, indicating the presence of the patient's hip or sacral region 724 at the location of the sensor 730(i), the electronics 750 compare the location of the sensor 730(i) generating the sensor signal to the location of the hip locator 712 and compute the migration distance d based on the difference between the sensor 730(i) location 714 and the location of the hip locator 712.

Figure 14:
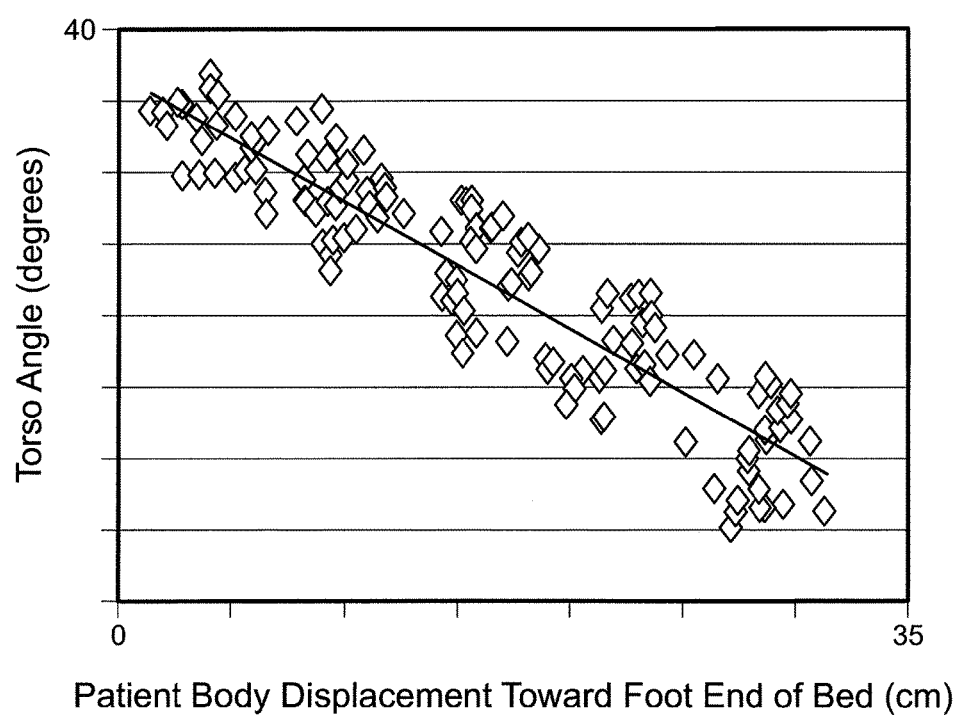
FIG. 14 is a simplified plot of data obtained through experimentation, illustrating a relationship between patient body displacement and torso angle.

The illustrative electronics 750 determine the patient's torso angle by mapping the migration distance d to torso angle values according to a relationship obtained through experimental results. This mapping can be performed using, for example, a mapping table, database lookup, a graphical plot, or a mathematical function representing the relationship between migration distance and torso angle. An example of a plot illustrating a relationship between migration distance and torso angle, which may be used by the electronics 750, is shown in FIG. 14. In FIG. 14, patient body displacement (e.g., migration) toward the end of the bed is measured in centimeters and plotted against the corresponding observed patient torso angle (measured in degrees). The plot of FIG. 14 illustrates a relationship in which the torso angle decreases as the patient body displacement increases, and vice versa.

In some embodiments, the sensor 730 is configured to monitor downward migration of the patient's head (e.g., movement toward the foot end 732) rather than migration of the patient's hip or sacral region 724. In these embodiments, the sensor 730 is coupled to the head section 716, the sensor 730 outputs sensor signals indicative of the actual location of the patient's head, and the torso angle electronics map the head migration information to the corresponding torso angle in a similar manner as described above.

The torso angle electronics 750 may be embodied as a simple integrated circuit, e.g., circuitry or processor that is built into the patient support apparatus 700, or as a component (e.g., a software, firmware, or hardware module) of a patient support apparatus control module or another computing device (including a mobile computing device such as a tablet or smartphone). The sensor 730 may communicate the sensor signals to the electronics 750 using any suitable data communication technique, including a wired connection (e.g., using a data bus or a network), a wireless connection, or an optical communication link. Similarly, the electronics 750 may communicate the torso angle data to one or more other devices (e.g., to a patient support apparatus control unit, a display, or a mobile computing device) using any suitable data communication mechanism, including wired, wireless, and/or optical connections.

Figure 8:
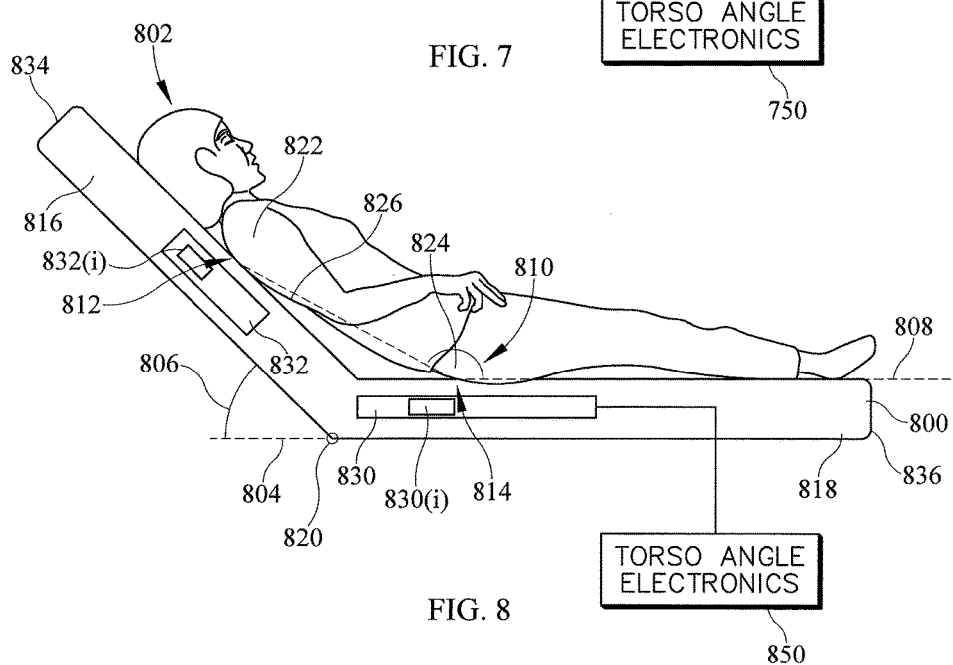
FIG. 8 is a simplified side elevational view of a patient positioned on a person support apparatus, schematically illustrating another embodiment of technology for determining the patient's torso angle.

Referring now to FIG. 8, another embodiment of technology for determining the patient's torso angle is shown. A patient 802 is positioned on a person support apparatus 800. The person support apparatus 800 has at least a lower torso or foot section 818 and an articulating head section 816. A distance between a head end 834 and a foot end 836 defines a length of the person support apparatus 800, e.g., a length of a support surface of the person support apparatus 800. The head section 816 is pivotable about a transverse axis of the person support apparatus 800, which extends into and out of the page at a pivot point 820. The head section 816 is illustratively elevated to a HOB angle 806 with respect to a horizontal axis 804 (e.g., a HOB angle of thirty degrees).

The person support apparatus 800 is equipped with a hip or sacral region sensor 830 and a number of shoulder sensors 832. The sensors 830, 832 each may be embodied similarly to the sensors 730, described above with reference to FIG. 7. The embodiment of FIG. 8 can estimate the patient's actual torso angle 810 using the outputs of the sensors 830, 832 rather than using the migration distance d. The person support apparatus 800 can estimate and monitor the patient's actual torso angle 810 at discrete time instances or continuously over a time interval. The patient's actual torso angle 810 is defined by an intersection of a plane 826, which extends from the patient's shoulders 822 to the patient's hips or sacral region 824, with a plane 808, which extends substantially horizontally away from the patient's hips or sacral region 824.

Each of the sensors 830, 832 outputs a sensor signal in response to phenomena indicating the presence of the patient's hip or sacral region (sensor 830) and each of the patient's shoulders (sensors 832) at the locations of the respective sensors 830, 832. Torso angle electronics 850 receive, pre-process as needed (e.g., perform analog-to-digital conversion, filtering, and/or other signal processing) and analyze the sensor signals. For example, the electronics 850 may access one or more data stores (not shown) to obtain information about the location of each of the respective sensors 830, 832, when the head section 816 of the person support apparatus 800 is positioned at various different HOB angles. When a signal from a particular sensor 830(i), 832(i) is received, indicating the presence of the patient's hip or sacral region 824 or shoulders 822, as the case may be, at the location of the sensor 830(i), 832(i), the torso angle electronics 850 computes an estimation of the patient's actual torso angle based on the locations of the sensors 830(i), 832(i) detecting the patient's hip or sacral region 824 and shoulders 822, and the HOB angle 806 at which the head section 816 is positioned. While not specifically shown, it should be understood that the HOB angle 806 may be detected by, e.g., an angle sensor, such as an inclinometer or accelerometer, coupled to the head section 816, and communicated to the torso angle electronics 850 by any suitable data communication mechanism, including any of the communication mechanisms mentioned in this disclosure.

In some embodiments, the pressure sensing elements 830(i), 832(i) are part of a pressure sensing array coupled to or supported by the person support apparatus 800, and the location of each of the pressure sensing elements 830(i), 832(i) at each degree of potential HOB articulation is established through testing or calibration (e.g., by gradually articulating the HOB from the minimum HOB angle to the maximum HOB angle, and recording the sensor location at each degree of articulation). In some embodiments, the location of the sensing elements is established in three-dimensional (3D) space (e.g., x, y, z coordinates) rather than two-dimensional (2D) (x, y) space. Use of 3D coordinates may provide greater accuracy. For example, if a patient is parallel to the longitudinal axis of the person support apparatus 800, the patient's effective torso angle is greater than if they are askew (lying diagonal in the bed). Including the third dimension in the location measurements can account for this difference. Whether the locations are measured in 2D or 3D space, the patient's torso angle 810 can be calculated based on the location of the patient's hip or sacral region 824 and shoulders 822 as indicated by the locations of the pressure sensing elements 830(i), 832(i) that have output the sensor signals.

The torso angle electronics 850 may be embodied as a simple integrated circuit, e.g., circuitry or processor that is built into the patient support apparatus 800, or as a component (e.g., a software, firmware, or hardware module) of a patient support apparatus control unit or another computing device (including a mobile computing device such as a tablet or smartphone). The sensors 830, 832 may communicate the sensor signals to the electronics 850 using any suitable data communication technique, including a wired connection (e.g., using a data bus or a network), a wireless connection, or an optical communication link. Similarly, the electronics 850 may communicate the torso angle data to one or more other devices (e.g., to a patient support apparatus control unit, a display, or a mobile computing device) using any suitable data communication mechanism, including wired, wireless, and/or optical connections.

Figure 9:
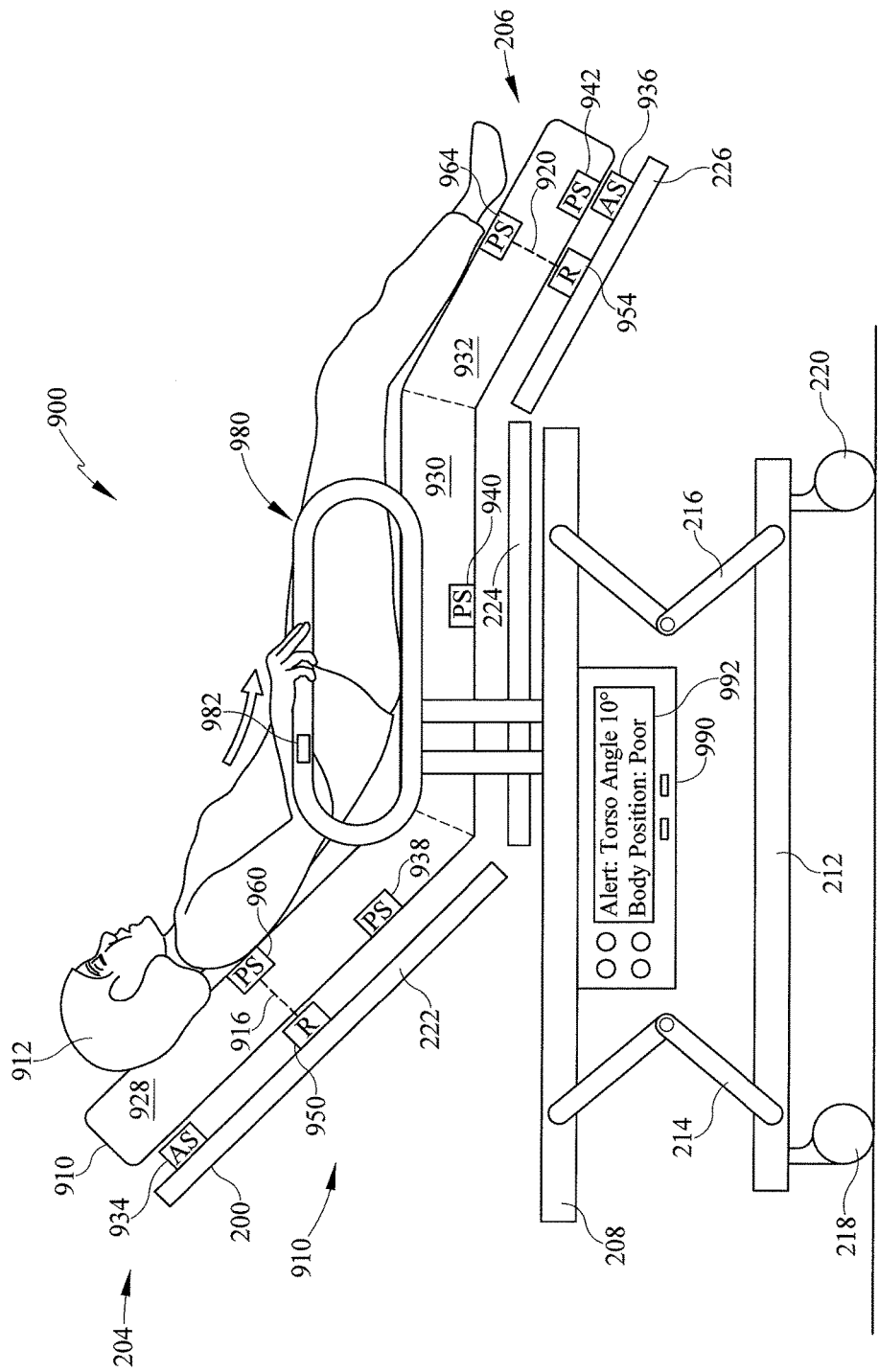
FIG. 9 is a simplified side elevational view of a person support system including a person support apparatus, showing a patient positioned on the person support apparatus, and showing some portions of the person support system schematically.

Referring now to FIG. 9, an illustrative person support apparatus 900 is shown in more detail. Features of the person support apparatus 700 described above and/or features of the person support apparatus 800 described above may be embodied in the person support apparatus 900. The person support apparatus 900 is shown in a chair-like position, but embodiments of the person support apparatus 900 may be designed to support a person in a laying-down position and/or a variety of other positions, as mentioned above. The illustrative person support apparatus 900 is of a type that is typically used in hospitals and/or other facilities in which health care is provided. However, aspects of this disclosure can be applied to any type of person support apparatus or similar structure configured with an articulating head section, including but not limited to beds, mattresses, surgical tables, stretchers, chairs, wheelchairs and other similar structures, whether or not all of the features of the illustrated person support apparatus 900 are included in such structure, and whether or not such person support structure includes other features not mentioned herein.

The person support apparatus 900 has a head end 204 and a foot end 206 longitudinally spaced from the head end 904. Components of the person support apparatus 900 may be embodied similarly to components of any of the person support apparatus 110, 700, or 800 described above, and in some cases the prior reference numerals are repeated in FIG. 9 for ease of discussion. A base 212 is movably supported by a pair of head end casters 218 (view of one caster obstructed) and a pair of foot end casters 220 (view of one caster obstructed). The casters 218, 220 each include one or more wheels that movably support the person support apparatus 900 relative to a floor or other surface, in one or more directions. A frame 208 is coupled to and supported by the base 212 by a lift mechanism, which includes a pair of head end lift arms 214 (view of one lift arm obstructed by the other) and a pair of foot end lift arms 216 (view of one lift arm obstructed by the other). The lift arms 214, 216 operate to raise, lower, and tilt the frame 208 relative to the base 212. A deck 200 is coupled to and supported by the frame 208. The deck 200 has a number of sections including, in the illustrated embodiment, an articulating head section 222, a seat section 224 (which may also articulate, in some embodiments) and an articulating foot section 226. At least the head section 222 and the foot section 226 pivot relative to the frame 208, either manually/mechanically or via a number of powered actuators (not shown) (such as electronic linear actuators or hydraulic cylinders).

Figure 10:
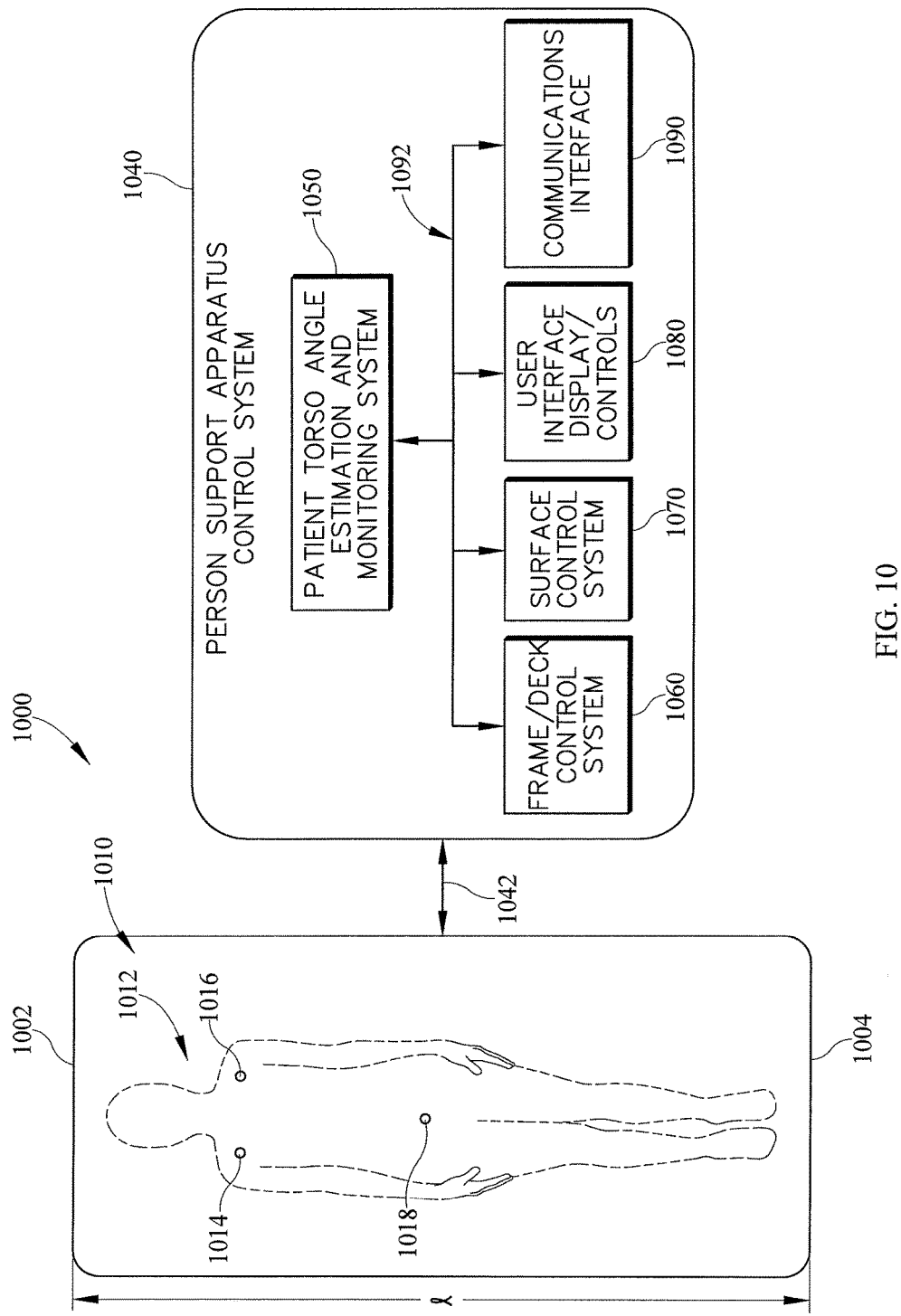
FIG. 10 is a simplified view of at least one embodiment of a person support system including a top plan view of a person support apparatus equipped with one or more body position sensors, showing a patient situated on the person support apparatus (in phantom), and a schematic depiction of at least one embodiment of a torso angle estimation and monitoring system in communication with one or more components of the person support apparatus.

In some embodiments, movement of the lift arms 214, 216 and/or pivoting of the deck sections 222, 224, 226 may be driven by actuators (not shown) that are controlled by a frame/deck control system (e.g., control system 1060, FIG. 10). Some examples of such actuators are such linear actuators or hydraulic cylinders that are responsive to electrical inputs, such as those disclosed in U.S. Pat. Nos. 5,715,548; 6,185,767; 6,336,235; 6,694,549; 7,454,805; 6,708,358; 7,325,265; 7,458,119; 7,523,515; 7,610,637; 7,610,638; and 7,784,128. In general, each of the actuators is coupled to a drive unit (e.g. a motor), which is responsive to control signals issued by the frame/deck control system 1060. When movement of the frame 208 or a deck section 222, 224, 226 is requested, the frame/deck control system (e.g., 1060) sends a corresponding control signal or signals to the appropriate drive unit to accomplish the requested movement.

The head and foot sections 222, 226 of the illustrative deck 200 are each equipped with an angle sensor or orientation sensor 934, 936, such as a ball switch, potentiometer, inclinometer, accelerometer, or the like, which detects changes in the orientation of the corresponding section 222, 226 of the deck 200 relative to another section of the person support apparatus 900. For example, the sensors 934, 936 may be used to determine the angle of the head section 222 and the foot section 226, respectively, relative to the frame 208 or to the horizontal. While not specifically shown, similar sensors may be coupled to the frame 208 and/or lift arms 214, 216, to determine the orientation of the frame 208 relative to the horizontal. The frame/deck control system (e.g., 1060) accesses computerized instructions, routines, or the like, which can determine, based on the output of the angle/orientation sensor or sensors, the orientation of the frame 208, the deck 200, and/or a deck section 222, 224, 226, as the case may be.

Also mounted to the illustrative head, seat, and foot sections 222, 224, 226, respectively, of the deck 200 are one or more readers/receivers 950, 954. The readers/receiver(s) 950, 954 can recognize and/or receive data signals transmitted wirelessly or optically by sensors 960, 964. As such, the readers/receiver(s) 950, 954 may be embodied as radio-frequency or infrared transceivers, for example. In some embodiments, the readers/receiver(s) 950, 954 may be configured to also recognize and/or receive data signals transmitted by position sensors 938, 940, 942. Each of the sensors

960, 964, 938, 940, 942 is coupled to or supported by a support surface 910. For instance, the sensors 960, 964, 938, 940, 942 may be installed adjacent a top portion of the each of the zones 928, 930, 932 of the surface 910. The readers/receiver(s) 950, 954, communicate the data signals output by the sensors 960, 964, 938, 940, 942 to the person support apparatus control system (e.g., 140 or 1040) via a communications link (e.g., 142, 1042). While multiple readers/receivers are shown in the illustrated embodiment, it should be understood that in some embodiments, a single reader/receiver may be used and in other embodiments, any number of readers/receivers may be used according to the requirements of a particular design or implementation of the person support apparatus 900. Moreover, the readers/receiver(s) 950, 954 may be placed in any suitable location or arrangement on the person support apparatus 900 (e.g., near the center or closer to the side edges, or both), including being mounted to the frame or installed in or on the surface 910, as it will be understood that the detection and control algorithms described herein can be adapted based on the locations of the readers/receiver(s) 950, 954 or the locations of the sensors 960, 964, 938, 940, 942.

The deck 200 supports the support surface 910 (e.g., a mattress), which, in turn, may support a patient 912 as shown. Each of the support zones 928, 930, 932 of the surface 910 may include a number of air bladders, foam, a combination thereof and/or other suitable materials. The zone 928 corresponds to the head section 222 of the deck 200, which is configured to support at least the head of the person 912; the zone 930 corresponds to the seat section 224 of the deck 200, which is configured to support at least a back, seat, thigh, and/or torso portion of the person 912; and the zone 232 corresponds to a foot section 226 of the deck 200, which is configured to support at least the legs and/or feet of the person 912. While only three zones are illustrated in FIG. 9, it should be understood that the surface 910 may include any number and configuration of support zones.

In embodiments where the surface 910 includes air bladders, each of the zones 928, 930, 932 includes at least one bladder that is operably coupled to a fluid supply (e.g., a blower) via one or more fluid conduits (e.g., plastic or flexible tubing). At least one pressure sensor 938, 940, 942 is operably coupled to the interior region of each of the zones 928, 930, 932 and/or the fluid conduit connected thereto. The pressure sensors 938, 940, 942 are configured to measure the internal fluid pressure in the zones 928, 930, 932 or individual bladders thereof, as the case may be. The pressure sensors 938, 940, 942 are operably coupled to a surface control system (e.g., 1070, FIG. 10) by a communications link, e.g., link 1042. As such, the surface control system 1070 can continuously monitor the internal air pressure of the zones 928, 930, 932 and interface with the fluid supply to adjust (e.g., increase or decrease) the internal air pressures according to one or more computerized air pressure control routines, which may include, for example, a routine for managing or relieving interface pressures between portions of the person's body and the person support surface 910, a routine for providing one or more pulmonary therapies (such as percussion or vibration), for alternating pressure increases and decreases in different zones or portions thereof (e.g., for lateral rotation or turning assistance), and/or other air pressure control routines.

Any or a subset of the sensors 960, 964, 938, 940, 942 may be configured to detect the location of the patient's hip or sacral region (724 or 824) and shoulders 722, 822 for purposes of computing the patient's torso angle using any of the methods described herein. For example, in some embodiments, some of the sensors 960, 964, 938, 940, 942 may be used to for multiple purposes, including pressure relief monitoring, patient position monitoring, and torso angle monitoring.

The person support apparatus 900 also includes a caregiver control unit 990, which is part of the user interface/controls sub-system 1080 (FIG. 10). The illustrative caregiver control unit 990 includes a graphical user interface 992 (e.g., a touchscreen display). The caregiver control unit 990 is, for simplicity, illustrated as being supported by the frame 208. In some embodiments, the caregiver control unit 990 may be integrated with one or more siderails or endboards (e.g., headboard or footboard) of the person support apparatus 900. Alternatively or in addition, the caregiver control unit 990 may be mounted to a wall, headwall, or other vertical structure, or may be embodied as a portable electronic device. In any case, the caregiver control unit 990 receives and processes electrical input (e.g. voltage) from one or more controls coupled thereto, which enable a caregiver to configure, activate and/or deactivate certain of the electronically-controllable functions of the person support apparatus 900. For example, some beds permit the caregiver to raise and lower the frame or change the position of certain deck sections, change the length or width of the frame or deck, to achieve a chair, CPR, Trendelenburg, or reverse Trendelenburg position, and/or to activate certain mattress therapies (such as lateral rotation, percussion, or vibration), by physically contacting the selected control. Such controls may include physical or virtual buttons, switches, dials, slides and the like. For instance, the illustrative caregiver control unit 990 includes a graphical touchscreen user interface 992, which has a display screen that can display text and/or graphics, and a number of physical or virtual interactive controls that allow a caregiver to activate, deactivate, or configure features of the person support apparatus 900. For example, the user interface 992 may present interactive controls that allow a caregiver to manually input an estimated amount of patient migration (e.g., based on an observed distance from the hip locator 712), which the system can then use to estimate the patient's torso angle. The caregiver control unit 990 includes circuitry to convey voltage generated by the interactive to the person support apparatus control module 1040.

Some examples of features and functions of the person support apparatus 900 that may be electronically controllable by the caregiver control unit 990 include, but are not limited to: adjusting the position, length, or width of the bed, raising, lowering, or pivoting a section or sections of the bed, weighing a person positioned on the bed, inflating, deflating, or adjusting inflation in one or more sections of the mattress, laterally rotating or turning a person positioned on the bed, providing percussion, vibration, pulsation, or alternating pressure therapy to a person positioned on the bed, adjusting airflow through a portion of a mattress or topper, enabling a person positioned on the bed to communicate with a caregiver located outside the person's room through an electrical network or telecommunications system, exchanging data and/or instructions with other devices, equipment, and/or computer systems (such as a nurse call system or healthcare facility workflow system), and/or other automated features. The above-described electronically controllable features of the person support apparatus 900 are intended to be illustrative and non-exhaustive. It will be understood that other electronically controllable features of the person support apparatus 900 not mentioned herein may be configured in accordance with a person's body position assessment. Although not specifically shown, it should be understood that the person support apparatus 900 has its own supply of electrical power (e.g. a battery) and/or a connector that connects the person support apparatus 900 to a supply of electrical current (e.g. a wall outlet), in order to power the electronically controllable features and functions of the person support apparatus 900.

In the illustration of FIG. 9, data signals from one or more of the sensors 960, 964, 938, 940, 942 have been processed by, e.g., the torso angle electronics 750, 850 and the electronics 750, 850 have computed the patient's torso angle as being only 10 degrees even though the HOB angle of the head section 222 is greater than 10 degrees. Accordingly, the electronics 750, 850 conclude that the person's overall body position is "poor," as shown by the display 992.

Referring now to FIG. 10, an illustrative person support system 1000 includes a person support apparatus 1010 and a person support apparatus control system 1040 communicatively coupled to the person support apparatus 1010. The person support apparatus 1010 has a head end 1002, a foot end 1004, and a length l between the head end 1002 and the foot end 1004. The person support apparatus 1010 is embodied as, for example, a hospital bed, a stretcher, or a similar device that can support a person in a horizontal position and/or one or more non-horizontal positions, including a position in which the person's head is elevated relative to the rest of the person's body. The person support apparatus control system 1040 and its subcomponents are embodied as hardware, software, or a combination of hardware and software, e.g. as a control module or a control unit. The control system 1040 controls one or more electronically-controllable features and/or functions of the person support apparatus 1010, such as deck articulation, mattress inflation/deflation, and the like.

The person support apparatus control system 1040 includes a patient torso angle estimation and monitoring system 1050, which is embodied as hardware, software, or a combination of hardware and software. The patient torso angle estimation and monitoring system 1050 is configured to estimate and monitor the actual torso angle of a patient 1012 situated on the person support apparatus 1010 using any of the techniques described herein including those discussed above with reference to FIGS. 7 and 8. To that end, the person support apparatus 1010 is equipped with a plurality of sensors 1014, 1016, 1018, which are configured in a similar manner to the sensors 832, 730, 830, described above. For instance, the sensors 1014, 1016, 1018 may be embodied as sensing elements of an "in-bed" pressure sensor array.

The person support apparatus control system 1040 can use the torso angle information computed by the torso angle estimation and monitoring system 1050 for a variety of different purposes. For example, the estimated patient torso angle computed by the patient torso angle estimation and monitoring system 1050 can be used to facilitate safe patient positioning. The computed patient torso angle can be displayed, e.g., on a graphical user interface located on a siderail of a person support apparatus. The computed torso angle can be transmitted to an electronic medical records (EMR) system for inclusion in the patient's medical record or for other reasons. The computed patient torso angle may be at least temporarily stored in computer memory of the person support apparatus and used, e.g., for protocol compliance evaluations, etc. The computed torso angle may be continuously estimated and used to activate an alarm if the torso angle falls below a threshold, e.g., a "safe" elevation.

Such a threshold can be input by, e.g., a caregiver using a user interface control 1080, or can be preset at a fixed value and stored in memory.

In some embodiments, the computed torso angle can be used to perform automated or semi-automated adjustment of the head section of the person support apparatus. For example, if the patient torso angle (which may be continuously estimated by the patient torso angle estimation and monitoring system 1050) falls below a threshold value, the person support apparatus may present an alarm or warning, and/or may provide instruction to the user (e.g., a caregiver), through an auditory instruction or visual instructions presented on the graphical user interface 1080. The user may be instructed to raise the HOB using a conventional HOB angle control mechanism (e.g., a frame/deck control of the user interface 1080 in communication with the frame/deck control system 1060), and the person support apparatus may output an audible or visual indicator when the patient is in a "safe" position. Alternatively, a button may be provided on the user interface 1080, which the user presses and holds to articulate the head section until the patient is in the desired position as determined by the torso angle algorithms of the torso angle estimation and monitoring system 1050.

In some embodiments, the person support apparatus control system 1040 monitors the person 1012's torso angle, based on data received from one or more of the sensors 1014, 1016, 1018, and uses that information to determine whether to adjust the position of the person support apparatus 1010 or adjust (e.g. turn on, turn off, or change a parameter of) a therapy feature of the person support apparatus 1010. In some embodiments, the person support apparatus control system 1040 uses data received from one or more of the sensors 1014, 1016, 1018 to determine whether the person 1012 has slid down in bed to the point that the slide-down event should be brought to the attention of, e.g., a caregiver, e.g., by electronic notification or alert. As used herein, "caregiver," may refer to any person that may care for or attend to the health or medical needs of the person 1012, such as a physician, therapist, nurse, family member or friend.

In more detail, the sensors 1014, 1016, 1018 may be embodied as any suitable type of inductive, resistive, or capacitive element (or any combination thereof). Some examples of such sensors include inclinometers, accelerometers, mag sensors, gyroscopes, and/or similar devices, which can be used to collect information about a person's position in space (e.g., the person's angle or position relative to gravity, the Earth's magnetic field, or some other point of reference). In some embodiments, output of one or more of the sensor(s) 1014, 1016, 1018 may be operably coupled to a radio transceiver, infrared transmitter, or similar mechanism. For example, the sensor(s) 1014, 1016, 1018 each may be integrated with an RFID (radio-frequency identification) tag or badge, to transmit the data signals from the respective sensors 1014, 1016, 1018 to the person support apparatus control system 1040 by a remote (e.g., radio frequency, optical, infrared, etc.) coupling. In general, the sensors 1014, 1016, 1018 and any sensor(s) with which the person support apparatus 1010 is equipped may output data signals in discrete or continuous, analog or digital form. The person support apparatus 1010 is equipped with appropriate signal processing circuitry and/or devices (e.g. analog-to-digital converters, digital-to-analog converters, filters, and the like) to enable the communication of signals between each of the sensors 1014, 1016, 1018 and the person support apparatus control system 1040 and the processing of the signals by the person support apparatus control system 1040.

The person support apparatus 1010 is in communication with the person support apparatus control system 1040 by a two-way data communication link 1042. The communication link 1042 may be embodied as, for example, any suitable type of wired, wireless, and/or optical connection or network, including a Controller Area Network and/or others. The illustrative person support apparatus control system 1040 is embodied as a number of computerized sub-systems, modules, programs, or the like, including the patient torso angle estimation and monitoring system 1050, the frame/deck control system 1060, the surface control system 1070, the user interface/controls sub-system 1080, and a communications interface 1090. The patient torso angle estimation and monitoring system 1050 analyzes the data signals received from the sensors 1014, 1016, 1018 using one or more of the methods described above. The frame/deck control system 1060 and the surface control system 1070 control electronically-controllable operational features of the person support apparatus 1010, such as head angle adjustment, foot angle adjustment, mattress pressure adjustment, etc., as described further below.

The user interface/controls sub-system 1080 provides a user-friendly interface by which a caregiver, the person 1012, or another authorized user can review data generated by the various modules of the person support apparatus control system 1040, including data generated by the patient torso angle estimation and monitoring system 1050, and adjust or configure the features and/or settings of the person support apparatus 1010 based on that data, as may be needed. For instance, the user interface/controls sub-system 1080 may process user-supplied inputs from a touch screen graphical display, a microphone, audio speakers, buttons, dials, slides, switches and the like, or any combination thereof and/or other suitable user control mechanisms. The communications interface 1090 enables the person support apparatus control system 1040 to communicate bi-directionally with other computing systems and/or devices, as described further below. In the illustrative person support apparatus control system 1040, the various modules and/or sub-systems 1050, 1060, 1070, 1080, 1090 are in data communication with each other as illustrated by the bi-directional communication link 1092. In this way, body position and/or torso angle data collected and analyzed by the patient torso angle estimation and monitoring system 1050, and/or notifications relating thereto, may be displayed or otherwise presented to a caregiver, incorporated into e.g. closed-loop control algorithms for the operation of the person support apparatus 1010, or transmitted to a remote device (such as a caregiver's mobile computing device, a nurse's station, or a similar device connected to a healthcare facility's nurse call system).

Figure 11A:
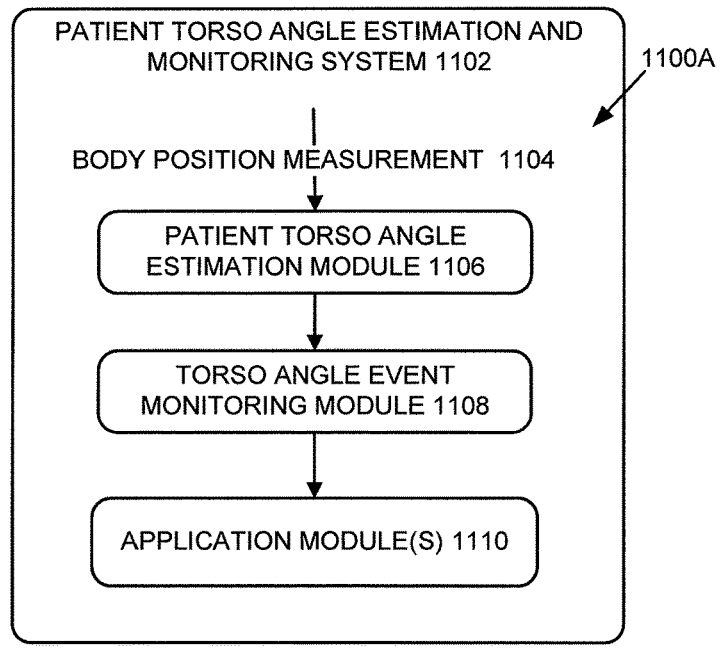
FIG. 11A is a simplified schematic diagram of an environment of at least one embodiment of the torso angle estimation and monitoring system of FIG. 10.

Referring now to FIG. 11A, an environment 1100A (e.g., a native or virtual runtime or "execution" environment) of an embodiment of a patient torso angle estimation and monitoring system 1102 is shown. The system 1102 may be embodied in, for example, the torso angle electronics 750, described above, or the person support apparatus control system 1040, described above. The system 1102 includes a number of computer executable instructions or modules illustratively represented by a patient torso angle estimation module 1106, a torso angle event monitoring module 1108, and a number of application modules 1110. The patient torso angle estimation module 1106 receives one or more body position measurements 1104. The body position measurements 1104 can include measurements that are indicative of the longitudinal displacement of a patient's body with respect to the length of a person support apparatus, e.g., the migrated distance d. The body position measurements 1104 may take the form of user input (e.g., a measurement made by visual observation of patient position in relation to a reference location, e.g., hip locator 712), sensed data (e.g., signals output by a sensor 730(i)), or a combination of user input and sensed data. The torso angle estimation module 1106 estimates the patient's actual torso angle with respect to the horizontal, based on the body position measurements 1104. To do this, the torso angle estimation module 1106 may utilize any of the techniques discussed above with reference to FIG. 7 or similar techniques. The torso angle event monitoring module 1108 compares the patient's torso angle as computed by the patient torso angle estimation module 1106 to a threshold value to determine if a torso angle event has occurred that indicates that the patient's position may need adjustment. The torso angle event monitoring module 1108 transmits torso angle event data to one or more application modules 1110 (e.g., a notification/alert module, an EMR update module, or a bed adjustment module).

Figure 11B:
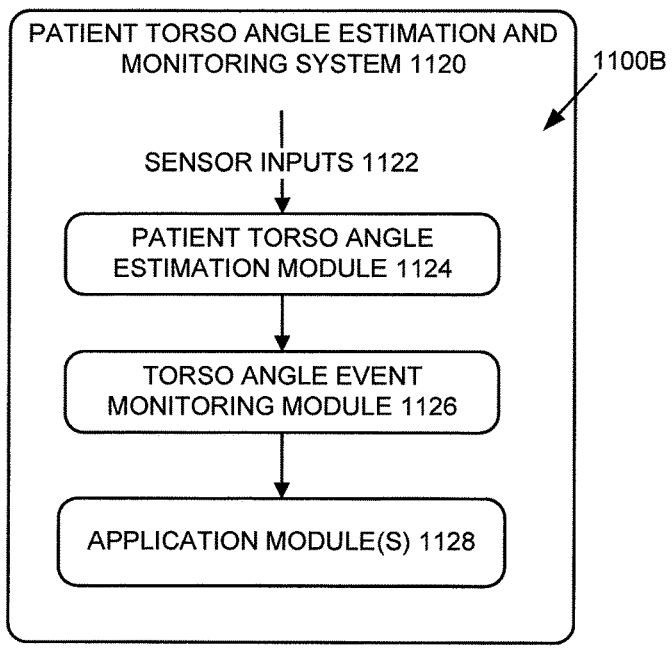
FIG. 11B is a simplified schematic diagram of an environment of another embodiment of the torso angle estimation and monitoring system of FIG. 10.

Referring now to FIG. 11B, an environment 1100B (e.g., a native or virtual runtime or "execution" environment) of an embodiment 1120 of a patient torso angle estimation and monitoring system is shown. The system 1120 may be embodied in, for example, the torso angle electronics 850, described above, or the person support apparatus control system 1040, described above. The system 1120 includes a number of computer executable instructions or modules illustratively represented by a patient torso angle estimation module 1124, a torso angle event monitoring module 1126, and a number of application modules 1128. The system 1120 is configured similarly to the system 1102 described above, except that the patient torso angle estimation module 1124 derives the estimation of the patient's actual torso value from sensor inputs 1122 using, e.g., one or more of the techniques described above with reference to FIG. 8. For example, the sensor inputs 1122 can be the outputs of the sensors 830, 832 shown in FIG. 8. The torso angle event monitoring module 1126 and application modules 1128 can be embodied similarly to the torso angle event monitoring module 1108 and the application modules 1110 mentioned above, so the description is not repeated here.

Figure 12A:
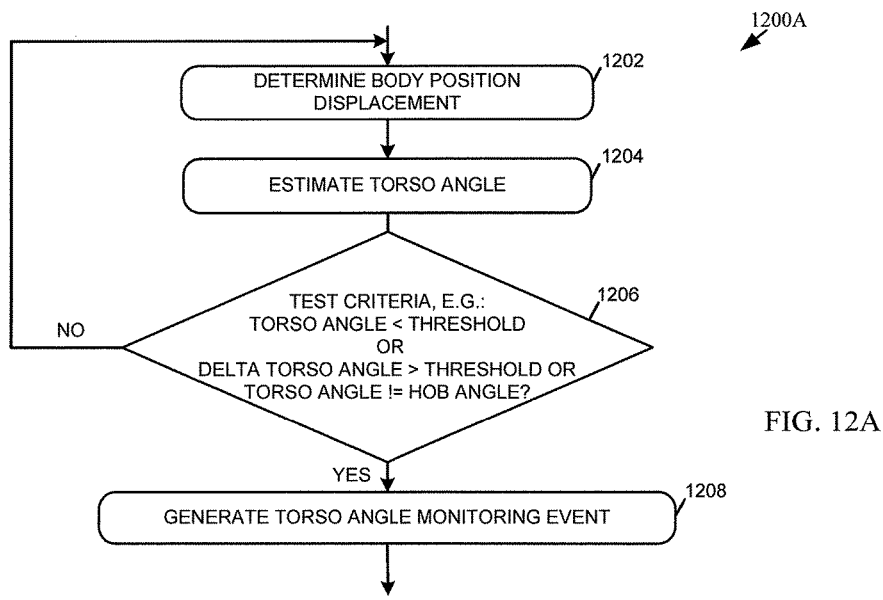
FIG. 12A is a simplified flow diagram of at least one embodiment of a method for monitoring patient torso angle.

Referring now to FIG. 12A, a method 1200A for in-bed monitoring of a patient's torso angle by a person support system (e.g., person support system 1000) is shown. The method 1200A may be embodied as computerized programs, routines, logic and/or instructions, which may be accessed by a processor, controller, or other computing device (e.g., as torso angle electronics 750 or control system 1040). At block 1202, the person support system determines a body position displacement of a person situated on a person support apparatus. To do this, the person support system uses any of the techniques described above with reference to FIG. 7 (e.g., comparing the person's actual position to a reference position). In block 1204, the person support system estimates the person's actual torso angle based on the body position displacement determined in block 1202.

In block 1206, the person support system tests the torso angle estimated in block 1204 against torso angle evaluation criteria, to determine whether an event warranting attention has occurred. For example, the person support system may compare the torso angle to a threshold value, or compare the change in torso angle over time to a threshold change in torso angle value, or compare the torso angle to the HOB angle. If the torso angle computed in block 1204 does not meet the threshold, or the change in torso angle exceeds a threshold amount or rate of change, or the torso angle does not substantially coincide with the HOB angle, or the torso angle does not meet some other applicable criteria, the patient support system proceeds to block 1208 and generates a torso angle monitoring event (e.g., display/annunciate an alert, transmit data to an EMR system or caregiver device, etc.). If the torso angle computed in block 1204 successfully satisfies the test criteria of block 1206, the patient support system may continue monitoring the body position displacement by returning to block 1202, or simply end the method 1200A.

Figure 12B:
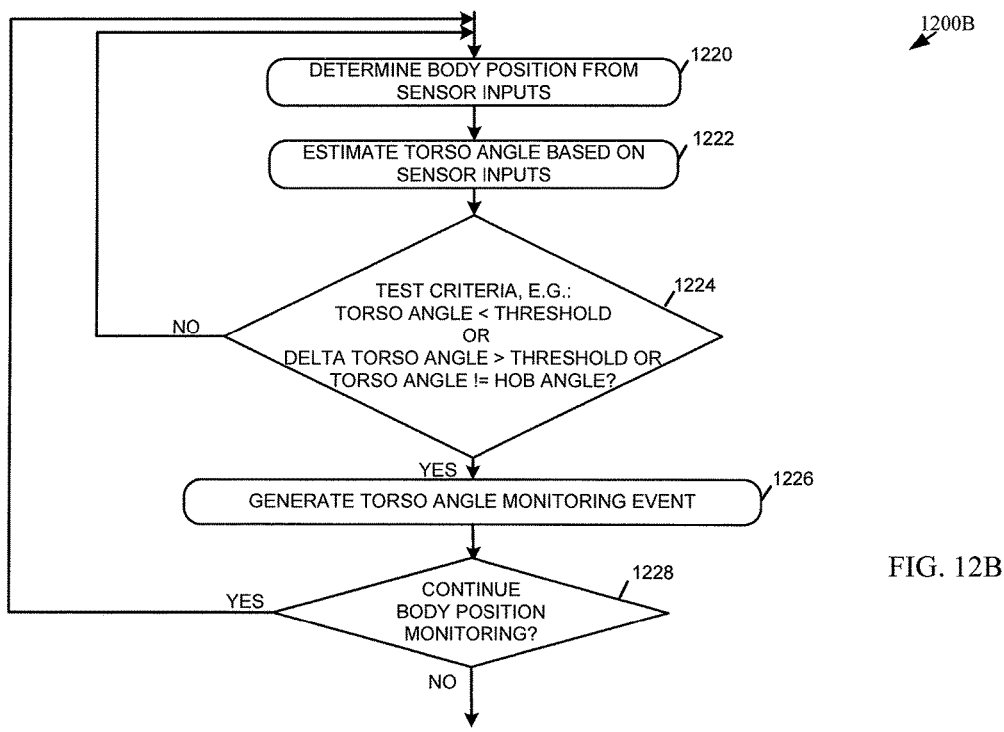
FIG. 12B is a simplified flow diagram of another embodiment of a method for monitoring patient torso angle.

Referring now to FIG. 12B, a method 1200B for in-bed monitoring of a patient's torso angle by a person support system (e.g., person support system 1000) is shown. The method 1200B may be embodied as computerized programs, routines, logic and/or instructions, which may be accessed by a processor, controller, or other computing device (e.g., as torso angle electronics 850 or control system 1040). At block 1220, the person support system determines a body position of a person situated on a person support apparatus. To do this, the person support system uses any of the techniques described above with reference to FIG. 8 (e.g., to obtain sensor inputs indicating the patient's shoulder and hip or sacral region locations. In block 1222, the person support system estimates the person's actual torso angle based on the location data derived from the sensor inputs, in block 1220 (e.g., by computing the torso angle from sensor inputs indicating the patient's shoulder and hip or sacral region locations, using a technique described above with reference to FIG. 8).

In block 1224, the person support system tests the torso angle estimated in block 1222 against torso angle evaluation criteria, to determine whether an event warranting attention has occurred. For example, the person support system may compare the torso angle to a threshold value, or compare the change in torso angle over time to a threshold change in torso angle value, or compare the torso angle to the HOB angle. If the torso angle computed in block 1222 does not meet the threshold, or the change in torso angle exceeds a threshold amount or rate of change, or the torso angle does not substantially coincide with the HOB angle, or the torso angle does not meet some other applicable criteria, the patient support system proceeds to block 1226 and generates a torso angle monitoring event (e.g., display/annunciate an alert, transmit data to an EMR system or caregiver device, etc.). If the torso angle computed in block 1222 successfully satisfies the test criteria of block 1226, the patient support system may continue monitoring the body position displacement by returning to block 1220, or simply end the method 1200B. Following block 1126, the patient support system may determine whether to continue monitoring the patient's body position and return to block 1220 if monitoring is to continue, or end the method 1200B, at block 1228.

Figure 13:
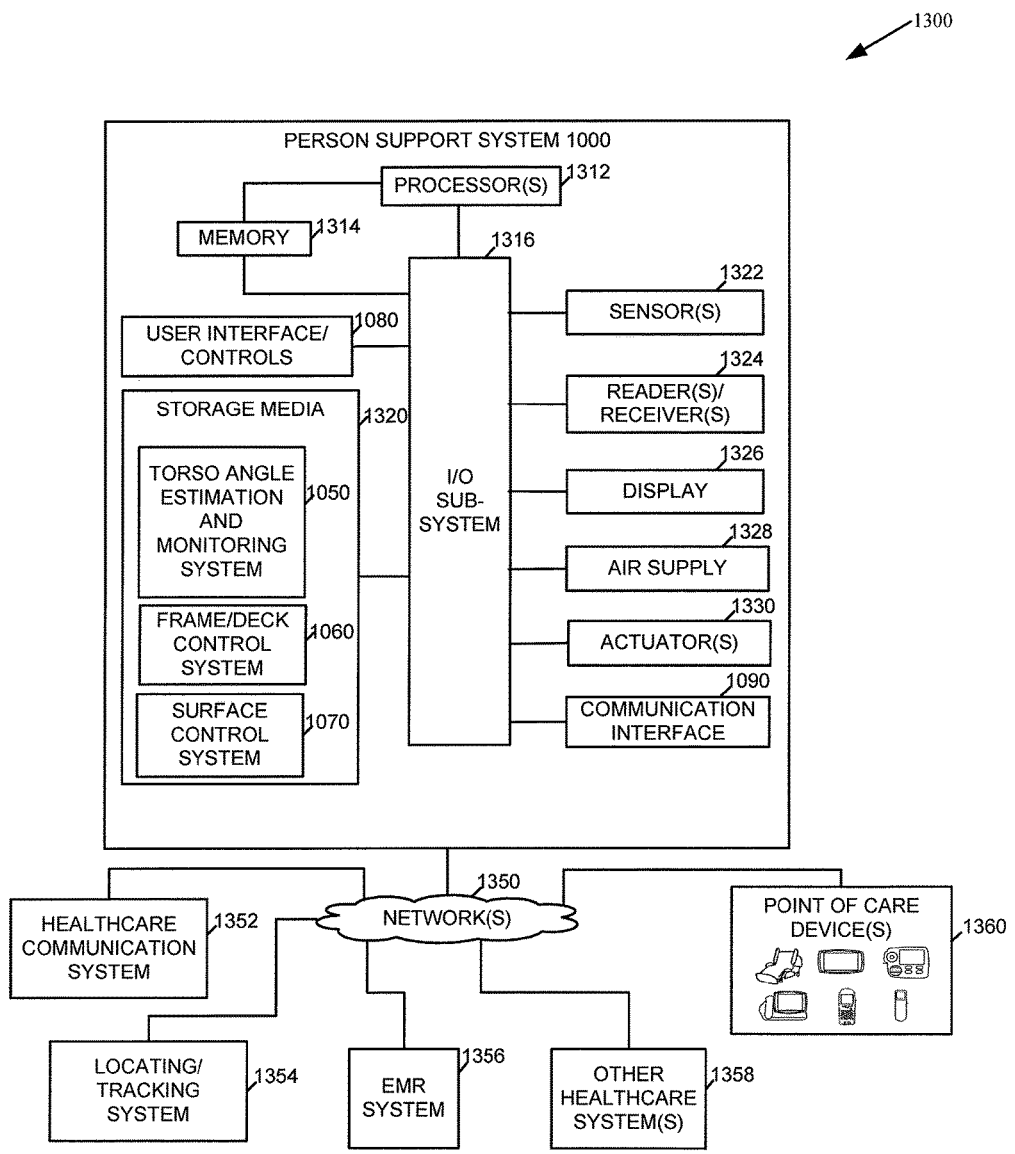
FIG. 13 is a simplified block diagram of at least one embodiment of a computing environment in which the person support system of FIG. 10 may be implemented.

Referring now to FIG. 13, a simplified block diagram of a hardware embodiment 1300 of the illustrative person support system 1000 is shown. In the illustrative embodiment 1300, the person support system 1000 is in communication with one or more other computing systems and/or devices 1352, 1354, 1356, 1358, 1360 via one or more networks 1350. Illustratively, the torso angle estimation and monitoring system 1050 is local to the person support system 1000, however, portions thereof may be distributed across one or more of the other computing systems and/or devices 1352, 1354, 1356, 1358, 1360 that are connected to the network(s) 1350.

The illustrative person support system 1000 includes a number of components, some of which are mounted to a person support apparatus (e.g., person support apparatus 700, 800, or 900), and others of which may be remotely coupled to the person support apparatus. The embodiment 1300 includes at least one processor 1312 (e.g. a microprocessor, microcontroller, digital signal processor, etc.), memory 1314, and an input/output (I/O) subsystem 1316. The person support system 1000 and/or portions thereof may be embodied in a control unit of the person support apparatus and/or any type of computing device including a point of care device such as a "nurse's station" or "patient station" of a nurse-call system, a mobile computing device, a server, a network of computers, or a combination of computers and/or other electronic devices.

The I/O subsystem 1316 typically includes, among other things, an I/O controller, a memory controller, and one or more I/O ports. The processor 1312 and the I/O subsystem 1316 are communicatively coupled to the memory 1314. The memory 1314 may be embodied as any type of suitable computer memory device (e.g., volatile memory such as various forms of random access memory).

The I/O subsystem 1316 is communicatively coupled to a number of hardware and/or software components including the user interface/controls 1080, one or more storage media 1320, one or more sensors 1322 (e.g., the sensors 730, 830, 832), one or more readers/receiver(s) 1324 (e.g., the readers/receiver(s) 950, 954), a display 1326 (e.g., the touchscreen display 992), an air supply 1328 (e.g., to control the supply of air to portions of the surface 910), one or more actuators 1330 (e.g., to control changes in position of the person support apparatus), and the communication interface 1090.

The storage media 1320 may include one or more hard drives or other suitable data storage devices (e.g., flash memory, memory cards, memory sticks, and/or others). In some embodiments, portions of the torso angle estimation and monitoring system 1050, the frame/deck control system 1060, and/or the surface control system 1070 reside at least temporarily in the storage media 1320. Portions of these systems 1050, 1060, 1070 may be copied to the memory 1314 during operation of the system 1000, for faster processing or other reasons.

The one or more networks 1350 may communicatively couple the person support system 1000 to a hospital or healthcare facility network, for example. Accordingly, the communication interface 1090 may include one or more wired or wireless network interface cards or adapters, for example, as may be needed pursuant to the specifications and/or design of the particular system 1000.

The other computing system and devices may include, for example, a healthcare communication system 1352 (e.g., a patient-nurse communication system), a locating and tracking system 1354 (e.g., a system that monitors the location of caregivers, patients, and/or equipment in a healthcare facility), an EMR system 1356, other healthcare system(s) 1358 (e.g., an admission, transfer and discharge system), and one or more point of care devices 1360 (e.g., other hospital equipment, communication devices, or medical devices). The person support system 1000 may include other components, sub-components, and devices not illustrated in FIG. 13 for clarity of the description. In general, the components of the person support system 1000 are communicatively coupled as shown in FIG. 13 by electronic signal paths, which may be embodied as any type of wired or wireless signal paths capable of facilitating communication between the respective devices and components.

In the foregoing description, numerous specific details, examples, and scenarios are set forth in order to provide a more thorough understanding of the present disclosure. It will be appreciated, however, that embodiments of the disclosure may be practiced without such specific details. Further, such examples and scenarios are provided for illustration, and are not intended to limit the disclosure in any way. Those of ordinary skill in the art, with the included descriptions, should be able to implement appropriate functionality without undue experimentation.

References in the specification to "an embodiment," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to effect such feature, structure, or characteristic in connection with other embodiments whether or not explicitly indicated.

Embodiments in accordance with the disclosure may be implemented in hardware, firmware, software, or any combination thereof. Embodiments may also be implemented as instructions stored using one or more machine-readable media, which may be read and executed by one or more processors. A machine-readable medium may include any mechanism for storing or transmitting information in a form readable by a machine. For example, a machine-readable medium may include any suitable form of volatile or non-volatile memory.

Modules, data structures, and the like defined herein are defined as such for ease of discussion, and are not intended to imply that any specific implementation details are required. For example, any of the described modules and/or data structures may be combined or divided into sub-modules, sub-processes or other units of computer code or data as may be required by a particular design or implementation of the system 100.

In the drawings, specific arrangements or orderings of schematic elements may be shown for ease of description. However, the specific ordering or arrangement of such elements is not meant to imply that a particular order or sequence of processing, or separation of processes, is required in all embodiments. In general, schematic elements used to represent instruction blocks or modules may be implemented using any suitable form of machine-readable instruction, and each such instruction may be implemented using any suitable programming language, library, application programming interface (API), and/or other software development tools or frameworks. Similarly, schematic elements used to represent data or information may be implemented using any suitable electronic arrangement or data structure. Further, some connections, relationships or associations between elements may be simplified or not shown in the drawings so as not to obscure the disclosure. This disclosure is to be considered as exemplary and not restrictive in character, and all changes and modifications that come within the spirit of the disclosure are desired to be protected.

The invention claimed is:

1. A person support apparatus comprising
a frame including a head section to support a person's upper body and a seat section to support the person's sacral region,
an angle sensor to sense an angle of elevation of the head section,
a hip position sensor to sense a distance, d, between a desired hip position and a measured hip position, and
electronics coupled to the angle sensor and to the hip position sensor, the electronics being configured to estimate the person's actual torso angle based on the angle of elevation of the head section as sensed by the angle sensor and the distance, d, as sensed by the hip position sensor.

2. The person support apparatus of claim 1, wherein the hip position sensor comprises a sensor array of individual sensing elements.

3. The person support apparatus of claim 2, wherein the individual sensing elements comprise resistive pressure sensors.

4. The person support apparatus of claim 1, wherein the hip position sensor is coupled to the seat section of the frame.

5. The person support apparatus of claim 1, further comprising a mattress supported by the frame, the hip position sensor being coupled to the mattress.

6. The person support apparatus of claim 5, wherein the hip position sensor is embedded in a seat zone of the mattress.

7. The person support apparatus of claim 5, wherein the hip position sensor is embedded in a mattress ticking of the mattress.

8. The person support apparatus of claim 1, further comprising a mattress supported by the frame and a mattress overlay atop the mattress, the hip position sensor being coupled to the mattress overlay.

9. The person support apparatus of claim 1, wherein the electronics uses mapping to estimate the person's actual torso angle.

10. The person support apparatus of claim 9, wherein the mapping is performed using a mapping table, a database lookup, a graphical plot, or a mathematical function.

11. The person support apparatus of claim 1, further comprising a shoulder position sensor to sense a position of the person's shoulders over the head section, the electronics being coupled to the shoulder sensor.

12. The person support apparatus of claim 11, wherein the electronics also uses the position of the person's shoulders as sensed by the shoulder position sensor in connection with estimating the person's actual torso angle.

13. The person support apparatus of claim 11, wherein the shoulder position sensor comprises a sensor array of individual sensing elements.

14. The person support apparatus of claim 13, wherein the individual sensing elements comprise resistive pressure sensors.

15. The person support apparatus of claim 11, wherein the shoulder position sensor is coupled to the head section of the frame.

16. The person support apparatus of claim 11, further comprising a mattress supported by the frame, the shoulder position sensor being coupled to the mattress.

17. The person support apparatus of claim 16, wherein the shoulder position sensor is embedded in a head zone of the mattress.

18. The person support apparatus of claim 16, wherein the shoulder position sensor is embedded in a mattress ticking of the mattress.

19. The person support apparatus of claim 11, further comprising a mattress supported by the frame and a mattress overlay atop the mattress, the shoulder position sensor being coupled to the mattress overlay.

20. The person support apparatus of claim 1, further comprising a graphical user interface (GUI) coupled to the electronics and configured to display information pertaining to the estimate of the person's actual torso angle.

* * * * *